United States Patent
Kori

(10) Patent No.: US 11,874,274 B2
(45) Date of Patent: Jan. 16, 2024

(54) SENSOR SUBSTRATE, METHOD FOR MANUFACTURING SAME, AND DETECTION DEVICE

(71) Applicant: Panasonic Intellectual Property Management Co., Ltd., Osaka (JP)

(72) Inventor: Shunsuke Kori, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 462 days.

(21) Appl. No.: 16/931,505

(22) Filed: Jul. 17, 2020

(65) Prior Publication Data
US 2020/0348297 A1    Nov. 5, 2020

Related U.S. Application Data

(63) Continuation of application No. PCT/JP2019/014461, filed on Apr. 1, 2019.

(30) Foreign Application Priority Data

Apr. 25, 2018 (JP) ................... 2018-084290
Apr. 25, 2018 (JP) ................... 2018-084303

(51) Int. Cl.
*G01N 33/68* (2006.01)
*G01N 33/563* (2006.01)
*G01N 33/543* (2006.01)

(52) U.S. Cl.
CPC ............... *G01N 33/54393* (2013.01); *G01N 33/54373* (2013.01)

(58) Field of Classification Search
CPC ............ G01N 33/5308; G01N 33/543; G01N 33/54373; G01N 33/54393;
(Continued)

(56) References Cited

U.S. PATENT DOCUMENTS

| 2008/0213910 A1 | 9/2008 | Jogikalmath |
| 2014/0030822 A1 | 1/2014 | Hataoka |
| 2017/0122940 A1 | 5/2017 | Kaneko et al. |

FOREIGN PATENT DOCUMENTS

| JP | 2005-140576 | 6/2005 |
| JP | 2008-309782 | 12/2008 |

(Continued)

OTHER PUBLICATIONS

Basu, A., Kunduru, K.R., Abtew, E., Domb, A.J. Polysaccharide-Based Conjugates for Biomedical Applications (2015).American Chemical Society. 26, 1396-1412. (Year: 2015).*

(Continued)

*Primary Examiner* — Christopher L Chin
*Assistant Examiner* — Estifanos Hailu
(74) *Attorney, Agent, or Firm* — Rimon P.C.

(57) ABSTRACT

The present disclosure provides a sensor substrate in which deterioration of a first specific-binding substance immobilized on a surface of the sensor substrate is suppressed even when the sensor substrate is washed or dried. The present sensor substrate includes a base material; a first specific-binding substance having a property of binding specifically to an analyte, the first specific-binding substance being immobilized on a surface of the base material; and a first sugar molecule. The first sugar molecule is immobilized on the surface of the base material by a chemical bond.

8 Claims, 24 Drawing Sheets

(58) Field of Classification Search
CPC ........... G01N 27/4145; G01N 33/5438; G01N 27/4146; G01N 33/573; G01N 33/551; G01N 33/48721; B81C 1/0206
USPC ...... 436/512, 516; 204/403.01; 257/27, 205, 257/49; 422/82.03, 82.01; 326/49, 68; 427/2.13, 338
See application file for complete search history.

(56) References Cited

FOREIGN PATENT DOCUMENTS

| | | | | |
|---|---|---|---|---|
| JP | 2010-508520 | 3/2010 | | |
| JP | 2010-164513 | 7/2010 | | |
| JP | 5929752 B | 6/2016 | | |
| WO | WO-2011111764 A1 * | 9/2011 | ....... | G01N 33/54393 |
| WO | 2012/168988 | 12/2012 | | |
| WO | 2015/194350 | 12/2015 | | |

OTHER PUBLICATIONS

Steinke et al.("Detection of diclofenac molecules by planar and nanostructured plasmonic sensor substrates", Sensors and Actuators B: Chemical, V 254, 749-754 (2018)). (Year: 2018).*
Metrology for the characterization of biomolecular interface for diagnostic devices. EMRP. V 1.0, 1-30, (2015) (Year: 2015).*
International Search Report of PCT application No. PCT/JP2019/014461 dated Jul. 2, 2019.

* cited by examiner

SENSOR SUBSTRATE, METHOD FOR MANUFACTURING SAME, AND DETECTION DEVICE

BACKGROUND

1. Technical Field

The present disclosure relates to a sensor substrate for detecting an analyte in a sample, a method for manufacturing the sensor substrate, and a detection device.

In recent years, biosensors using physiologically active substances (hereinafter, referred to as specific-binding substances) such as antibodies have been used in fields of medicine and biotechnology. The specific-binding substances are susceptible to damage by heat or drying. For example, a part of a structure of the specific-binding substance is denatured by heat or drying to lower the function of the specific-binding substance. This often causes a problem in a case where a specific-binding substance immobilized on the surface of the sensor substrate is used.

To solve the problem, Patent Literature 1 discloses a sensor substrate in which a surface of the sensor substrate is coated with a storage solution including a saccharide and a non-specific protein that does not have a property of binding to a specific-binding substance (hereinafter, such a non-specific protein is referred to as a non-specific-binding substance). In the sensor substrate, since the specific-binding substance on the surface of the sensor substrate is coated with the storage solution, the specific-binding substance is protected from drying, and the function (activity) of the specific-binding substance is prevented from being lowered.

CITATION LIST

Patent Literature

Patent Literature 1: Japanese Patent Publication No. 5929752

SUMMARY

However, since the surface of the above conventional sensor substrate is coated only with the storage solution, when the sensor substrate is washed, the storage solution flows from the surface of the sensor substrate, and when the sensor substrate is dried, the moisture in the storage solution is evaporated. As a result, when the conventional sensor substrate is washed or dried, the effect of protecting the surface of the sensor substrate from being dried is not sufficiently maintained. In particular, structural and functional deterioration of the specific-binding substance (hereinafter, referred to as deterioration of the specific-binding substance) causes a problem that an amount of a contaminant in the sample bound non-specifically to the deteriorated part of the specific-binding substance is increased. Hereinafter, such a binding of the non-specific binding of the contaminant is referred to as non-specific adsorption.

To solve the problem, the present disclosure provides a sensor substrate and a method for manufacturing the sensor substrate in which deterioration of the first specific-binding substance immobilized on the surface of the sensor substrate is suppressed even when the sensor substrate is washed or dried. Moreover, the present disclosure provides a detection device for detecting an analyte accurately by using the sensor substrate.

To solve the problem, the sensor substrate according to one aspect of the present disclosure comprises:

a base material;

a first specific-binding substance that has a property of binding specifically to an analyte and is immobilized on a surface of the base material; and a first sugar molecule, wherein the first sugar molecule is immobilized by a chemical bond on the surface of the base material.

In addition, the method for manufacturing a sensor substrate according to one aspect of the present disclosure comprises:

preparing a base material; and immobilizing a first specific-binding substance capable of binding specifically to an analyte on a surface of the base material, and immobilizing a first sugar molecule by a chemical bond on the surface of the base material.

In addition, the detection device according to one aspect of the present disclosure comprises:

any one of the above sensor substrate;

an introduction part through which a second specific-binding substance and a sample are introduced to the sensor substrate, wherein the second specific-binding substance has a property of binding specifically to an analyte and is labeled with a labeled substance, and the sample contains the analyte;

an application part for applying an inducer capable of inciting a signal from the labeled substance to the sensor substrate to which the second specific-binding substance and the sample have been introduced; and a detection part for detecting the analyte on the basis of the signal emitted from the labeled substance.

According to the present disclosure, provided is a sensor substrate and a method for manufacturing the sensor substrate in which deterioration of the first specific-binding substance immobilized on the surface of the sensor substrate is suppressed even when the sensor substrate is washed or dried. Moreover, according to the present disclosure, the detection device for detecting an analyte accurately is provided.

DETAILED DESCRIPTION OF THE EMBODIMENTS

Figure 1:
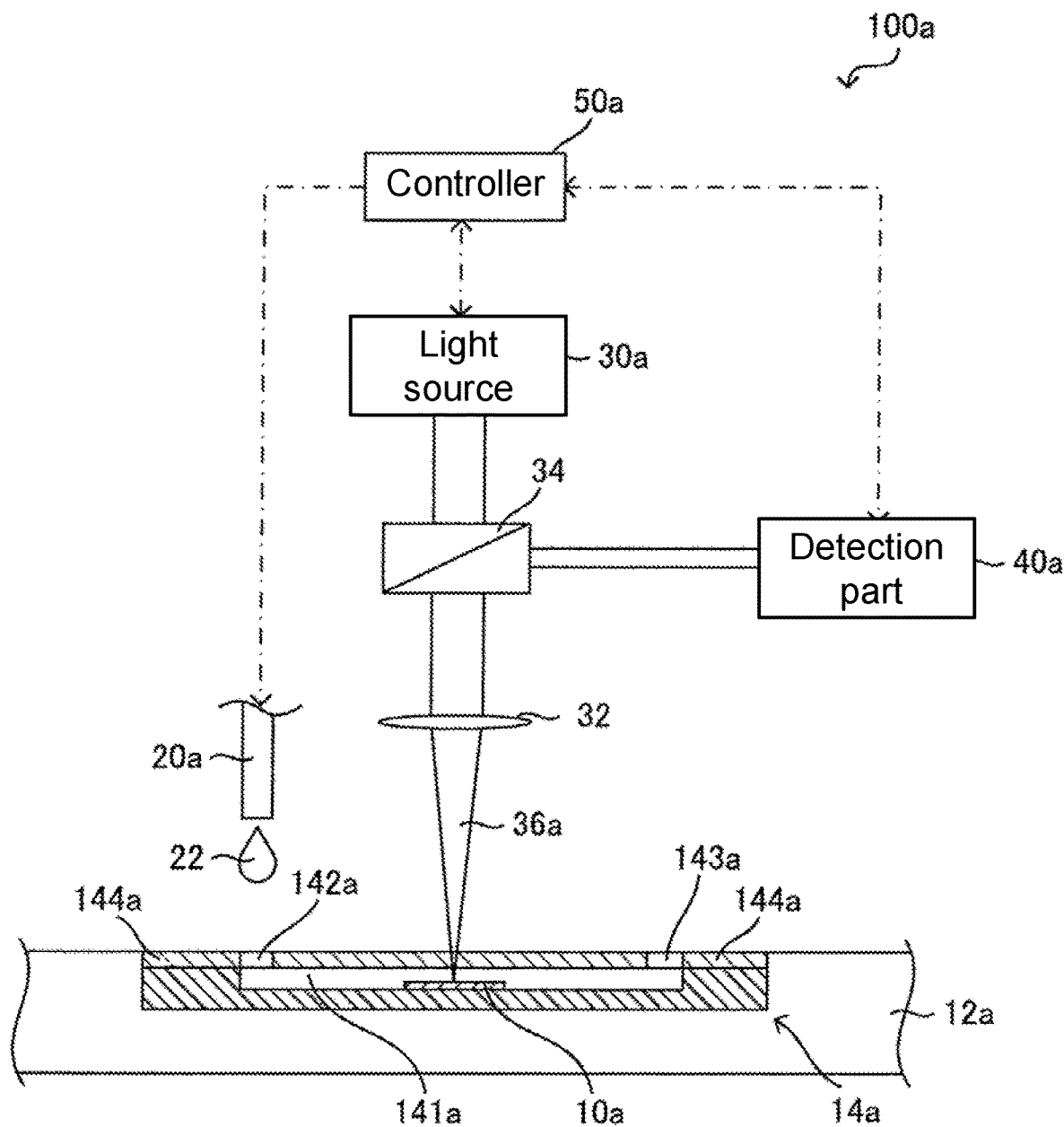
FIG. 1 is a schematic configuration diagram showing one example of a detection device according to a first embodiment.

The outline of one aspect of the present disclosure will be described below.

The sensor substrate according to one aspect of the present disclosure comprises:

a base material;

a first specific-binding substance that has a property of binding specifically to an analyte and is immobilized on a surface of the base material; and a first sugar molecule, wherein the first sugar molecule is immobilized by a chemical bond on the surface of the base material.

In the above sensor substrate, even if the sensor substrate is washed, since the first sugar molecule does not flow from the surface of the sensor substrate, the surface of the sensor substrate is less likely to be dried due to the water-holding ability of the first sugar molecule. In addition, even when the sensor substrate is dried, the surface of the sensor substrate is less likely to be dried, since the first sugar molecule has the water-holding ability. As a result, the first specific-binding substance is less likely to be damaged by the drying. Therefore, even when the sensor substrate is washed or dried, deterioration of the first specific-binding substance immobilized on the surface of the sensor substrate is suppressed.

For example, in the sensor substrate according to one aspect of the present disclosure, the base material may include a substrate and an organic membrane disposed on the substrate;

the first specific-binding substance may be immobilized on the surface of the base material through binding to the organic membrane; and the first sugar molecule may be immobilized on the organic membrane by the chemical bond.

In the above sensor substrate, the first specific-binding substance and the first sugar molecule are stably immobilized on the surface of the base material. The first sugar molecule immobilized stably on the surface of the base material is likely to remain without being separated from the surface, even when the sensor substrate is washed. Since a hydroxyl group (OH group) which the first sugar molecule has acts in place of a water molecule, even when the sensor substrate is dried, the deterioration of the first specific-binding substance due to the drying is suppressed.

For example, in the sensor substrate according to one aspect of the present disclosure, the organic membrane may be a self-assembled monolayer.

In the above sensor substrate, the first specific-binding substance and the first sugar molecule can easily form a chemical bond with the organic membrane. Therefore, the first specific-binding substance and the first sugar molecule are immobilized stably on the surface of the base material.

For example, in the sensor substrate according to one aspect of the present disclosure, the chemical bond may be an amide bond.

In the above sensor substrate, the first sugar molecule is immobilized by an amide bond that is a covalent bond with the organic membrane. Covalent bonds have strong bonding strength among chemical bonds. Therefore, the first sugar molecule is immobilized stably on the surface of the base material. The water-holding ability of the first sugar molecule immobilized stably in this way protects the surface of the sensor substrate from being dried and suppresses structural and functional deterioration of the first specific-binding substance. In this way, storage stability of the sensor substrate can be improved.

For example, the sensor substrate according to one aspect of the present disclosure may include a blocking agent covering at least a part of the surface of the base material.

In the above sensor substrate, when the analyte is detected, non-specific bonding or adsorption (hereinafter, non-specific adsorption) of the contaminant on the surface of the base material can be suppressed. Therefore, noise generated by the non-specific adsorption (namely, non-specific adsorption noise) is suppressed, and the analyte can be detected accurately.

For example, the sensor substrate according to one aspect of the present disclosure may include a second sugar molecule, wherein the second sugar molecule may be disposed at least on a surface of the first specific-binding substance.

In the above sensor substrate, since the second sugar molecule is disposed at least on the surface of the first specific-binding substance, and the first sugar molecule is disposed on the surface of the base material, the surface of the first specific-binding substance, namely, not only a binding site where the first specific-binding substance binds to the analyte but also a part of the first specific-binding substance close to the surface of the base material can be protected from be dried. As just described, the entire surface of the first specific-binding substance is protected from being dried, and the deterioration of the first specific-binding substance due to the drying is suppressed. Further, by disposing the first sugar molecule on the surface of the base material, it is possible to suppress non-specific-binding of a contaminant and a labeled antibody in the sample on the surface of the base material. As just described, even if the sensor substrate is stored, since the deterioration of the first specific-binding substance is suppressed and the non-specific adsorption is suppressed, the storage stability of the sensor substrate is improved.

For example, in the sensor substrate according to one aspect of the present disclosure, the second sugar molecule may have a chemical structure different from that of the first sugar molecule.

By using sugar molecules having different chemical structures from each other, namely, different types of sugar molecules, a sensor substrate having a desired storage stability can be provided, depending on a design such as a specific-binding substance, a configuration of the base material and the organic membrane, the analyte, or a detection method.

In addition, a method for manufacturing a sensor substrate according to one aspect of the present disclosure comprises:
preparing a base material; and
immobilizing a first specific-binding substance capable of binding specifically to an analyte on a surface of the base material, and immobilizing a first sugar molecule by a chemical bond on the surface of the base material.

In the above manufacturing method, a sensor substrate can be provided in which the deterioration of the first specific-binding substance due to the drying can suppressed even when the sensor substrate is washed or dried.

In addition, the detection device according to one aspect of the present disclosure comprises:
any one of the above sensor substrate;
an introduction part through which a second specific-binding substance and a sample are introduced to the sensor substrate, wherein the second specific-binding substance has a property of binding specifically to an analyte and is labeled with a labeled substance, and the sample contains the analyte;
an application part for applying an inducer capable of inciting a signal from the labeled substance to the sensor substrate to which the second specific-binding substance and the sample have been introduced; and
a detection part for detecting the analyte on the basis of the signal emitted from the labeled substance.

The above detection device can detect the analyte accurately.

These comprehensive or specific aspects may be realized by a system, a method, an integrated circuit, a computer program, or a computer-readable recording medium such as a CD-ROM. These comprehensive or specific aspects may be realized by arbitrary combination of the system, the method, the integrated circuit, the computer program, or the recording medium.

Hereinafter, embodiments of the present disclosure will be specifically described with reference to the drawings.

It should be noted that each of the embodiments described below shows a comprehensive or specific example. Numerical values, shapes, materials, constituent elements, arrangement positions and connection forms of constituent elements, steps, and order of steps shown in the following embodiments are merely examples, and are not intended to limit the present disclosure. In addition, among the constituent elements in the following embodiments, constituent elements that are not described in the independent claims indicating the highest concept are described as optional constituent elements.

In addition, the drawings are not necessarily shown accurately. In each drawing, substantially the same configuration is denoted by the same reference numeral, and redundant description is omitted or simplified.

First Embodiment

[Configuration of Detection Device]

FIG. 1 is a schematic configuration diagram showing one example of a detection device 100a according to the present embodiment.

As shown in FIG. 1, the detection device 100a comprises a sensor substrate 10a, an introduction part 20a, an application part 30a (here, a light source 30a), a detection part 40a, and a controller 50a. In the present embodiment, the detection device 100a further comprises a sensor device 12a, a lens 32, and a beam splitter 34. In the present embodiment, the detection device 100a is a device for detecting an amount of an analyte optically, for example. The detection method will be described by taking a surface-enhanced fluorescence method as an example. Hereinafter, each constituent element of the detection device 100a will be described.

The sensor device 12a comprises a sensor cell 14a. In FIG. 1, the sensor device 12a comprises a single sensor cell 14a; however, the sensor device may comprise a plurality of sensor cells. If the sensor device comprises the plurality of the sensor cells, a mechanism for moving the sensor device may be provided in such a manner that the plurality of the sensor cells are individually irradiated with excitation light 36a.

The sensor cell 14a comprises the sensor substrate 10a, a flow path 141a, and a lid part 144a having a supply hole 142a and a discharge hole 143a. The lid part 144a comprises, for example, the supply hole 142a through which a sample liquid 22, a cleaning liquid, and a solution including a second antibody are supplied into the sensor cell 14a, and a discharge hole 143a through which the sample liquid 22 supplied into the sensor cell 14a is discharged to the outside. The lid part 144a is formed of, for example, a material having optical transparency such as glass or resin. In addition, the positions of the supply hole 142a and the discharge hole 143a are not specifically limited. The supply hole 142a and the discharge hole 143a may be positioned suitably at a desired position, depending on the design.

The flow path 141a is a path for guiding the sample liquid 22 supplied from the supply hole 142a to the sensor substrate 10a. Although FIG. 1 shows an example in which the sensor substrate 10a is disposed in the flow path 141a, the sensor substrate 10a may be formed integrally with the flow path 141a. In other words, the sensor substrate 10a may be directly formed on the bottom part of the flow path 141a.

Figure 2:
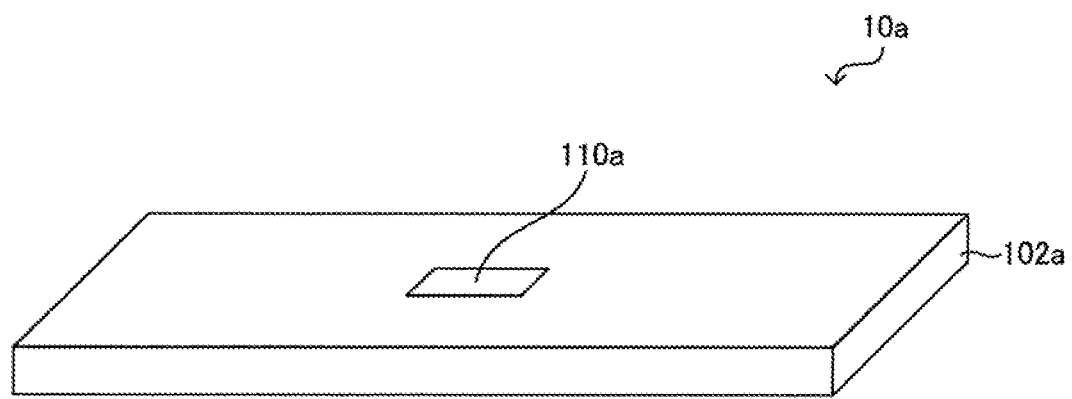
FIG. 2 is a perspective view showing one example of a sensor substrate in the first embodiment.

FIG. 2 is a perspective view showing one example of the sensor substrate 10a according to the present embodiment. In the sensor substrate 10a, a first specific-binding substance having a property of binding specifically to an analyte is immobilized on at least a part of the surface of the base material 102a, and a region where a first sugar molecule is immobilized by a chemical bond is formed on the at least the part of the surface of the base material 102a. Hereinafter, the region is referred to as a detection region 110a. Details of the sensor substrate 10a will be described later.

The introduction part 20a introduces a second specific-binding substance and a sample into the sensor cell 14a. Specifically, the sample liquid 22 including the second specific-binding substance and the sample is dropped through the introduction part 20a into the supply hole 142a provided in the sensor cell 14a. More specifically, the introduction part 20a may include, for example, a pump (not shown) and a valve (not shown). In this case, the introduction part 20a may introduce the sample liquid 22 into the sensor substrate 10a by opening the valve and operating the pump.

The second specific-binding substance has a property of binding specifically to the analyte, and is labeled with a labeled substance (for example, a fluorescent substance). The sample is a liquid that may contain an analyte.

If the sample contains an analyte, the analyte binds to the first specific-binding substance immobilized on the surface of the base material of the sensor substrate 10a. In other words, a composite of the first specific-binding substance, the analyte, the second specific-binding substance, and the fluorescent substance is bound to the surface of the base material. In this state, if the sensor substrate 10a is irradiated with light, fluorescence is emitted from the fluorescent substance that has been indirectly bound to the analyte via the second specific-binding substance.

The light source 30a is one example of an application part, and emits excitation light 36a, which is substantially parallel light, with which the sensor substrate 10a is irradiated. The application part applies an inducer 36a (here, excitation light 36a) for inducing a signal from the labeled substance to the sensor substrate 10a into which the second specific-binding substance labeled with the labeled substance and the sample have been introduced. When the sensor cell 14a is irradiated with the excitation light 36a, the excitation light 36a passes through the lid part 144a formed of the material having optical transparency as described above, and reaches the detection region 110a of the sensor substrate 10a. For the light source 30a, a publically known technique can be used without any particular limitation. An example of the light source 30a is a laser such as a semiconductor laser or a gas laser. Preferably, the light source 30a emits the excitation light having a wavelength having a small interaction with a substance contained in the virus (for example, 400 nm to 2,000 nm). Furthermore, the wavelength of the excitation light is preferably 600 nm to 850 nm, which can be used by the semiconductor laser.

The beam splitter 34 splits the surface-enhanced fluorescence generated in the detection region 110a from the excitation light 36a emitted from the light source 30a. Specifically, the excitation light 36a from the light source 30a passes through the beam splitter 34, and the beam splitter 34 splits the surface-enhanced fluorescence generated in the sensor cell 14a and guides it to the detection part 40a.

The lens 32 condenses the excitation light 36a from the light source 30a that has passed through the beam splitter 34 into the detection region 110a.

The detection part 40a splits the surface-enhanced fluorescence guided by the beam splitter 34, and outputs an electric signal which corresponds to the amount of the analyte in the sample by detecting light in a specific wavelength band. The detection part 40a can use a publically known technique without particular limitation, as long as the detection part 40a can detect light in a specific wavelength band. For example, as the detection part 40a, an interference filter through which a specific wavelength band passes in order to split light, a Czerny spectroscope for performing spectroscopic analysis using a diffraction grating, and an echelle spectroscope can be used. Further, the detection part 40a may include a notch filter for removing the excitation light 36a from the light source 30a, or a long pass filter by which the excitation light 36a from the light source 30a is blocked and through which the surface-enhanced fluorescence generated in the sensor cell 14a passes.

The controller 50a comprises a processor and a memory, and is realized by the processor executing a software program stored in the memory. In addition, the controller 50a is realized by one or more dedicated electronic circuits. The one or more dedicated electronic circuits may be integrated on one chip, or may be individually formed on a plurality of chips. The controller 50a analyzes the output signal of the detection part 40a to calculate the concentration of the analyte. Furthermore, the controller 50a controls the light source 30a and the introduction part 20a.

The detection part 40a and the controller 50a are one example of the detection part, and detect an analyte on the basis of fluorescence generated from the fluorescent substance by irradiation with excitation light.

[Configuration of Sensor Substrate]

FIG. 2 is a perspective view of the sensor substrate 10a which is one example of the sensor substrate according to the present embodiment. FIG. 3 is a cross-sectional view schematically showing a part of the sensor substrate 10a shown in FIG. 2 (here, a part of the detection region 110a). In the subsequent drawings, the same constituent elements as those in FIG. 3 are denoted by the same reference numerals, and description thereof is omitted.

In FIG. 2, the detection region 110a is formed on a part of the surface of the base material 102a; however, the shape of the detection region 110a and a ratio shown on the surface of the base material 102a are not limited to the illustration. For example, the detection region 110a may be formed on the entire surface of the base material 102a.

Figure 3A:
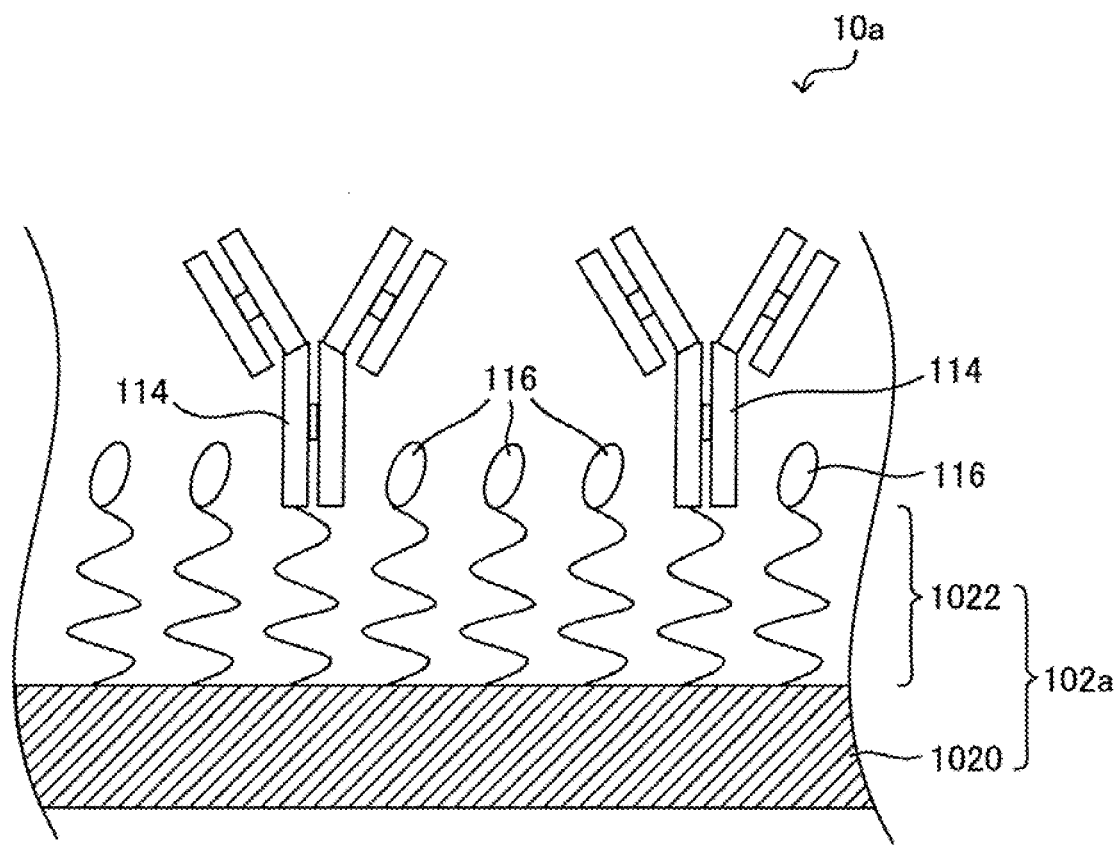
FIG. 3A is a cross-sectional view of one example schematically showing a part of the sensor substrate shown in FIG. 2.

As shown in FIG. 3A, the sensor substrate 10a comprises the base material 102a, a first specific-binding substance 114, and a first sugar molecule 116. The first specific-binding substance 114 has a property of binding specifically to the analyte, and is immobilized on the surface of the base material 102a. In addition, the first sugar molecule 116 is immobilized on the surface of the base material 102a by a chemical bond.

Figure 3B:
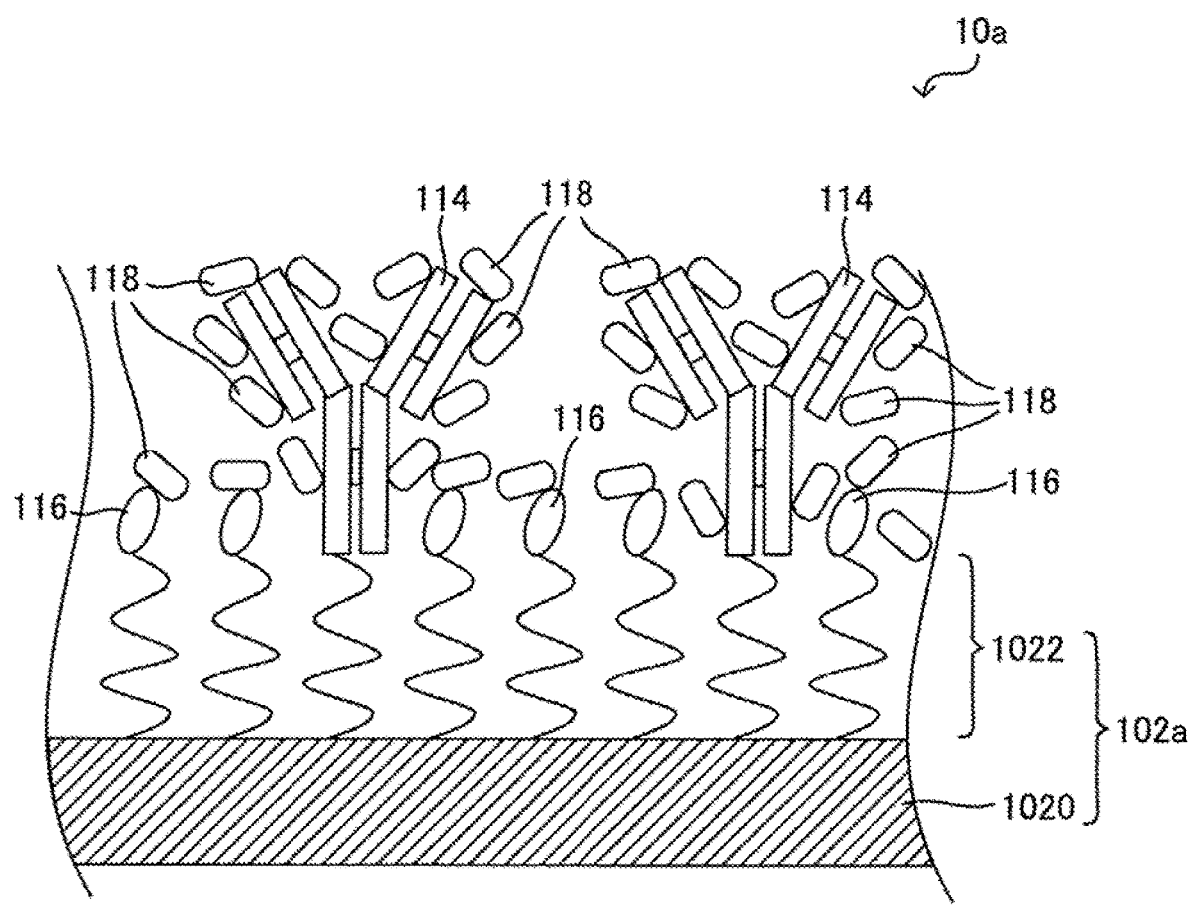
FIG. 3B is a cross-sectional view of another example schematically showing a part of the sensor substrate shown in FIG. 2.

As shown in FIG. 3B, the sensor substrate 10a may further comprise a second sugar molecule 118. The second sugar molecule 118 is disposed at least on the surface of the first specific-binding substance 114.

The shape and material of the base material 102a are not particularly limited, as long as the first specific-binding substance 114 and the first sugar molecule 116 can be bound to the surface of the base material 102a. Examples of the shape of the base material 102a include a particle shape, a fiber shape, a membrane shape, a sheet shape, a plate shape, and a flat shape. Examples of the material of the base material 102a include inorganic materials such as quartz, glass, silica, and ceramics, resins such as polycarbonate and cycloolefin polymer, natural materials such as hydrogel, agarose, cellulose, and latex, and metal materials such as gold, alumina, and silver. In addition, using a publically known surface treatment technique, a functional group such as an amino group, a carboxyl group, or a vinyl group may be appropriately introduced onto the surface of the base material 102a. In this case, the first specific-binding substance 114 and the first sugar molecule 116 can be easily bound to the surface of the base material 102a.

If the sensor substrate 10a is used as a plasmon excitation sensor, the base material 102a may have a metal thin film including at least one kind of metal such as silver, aluminum, copper, platinum, or an alloy of these metals on the surface of a support (substrate 1020 in FIG. 3) such as quartz, glass, polycarbonate resin, or cycloolefin polymer resin. Furthermore, the base material 102a may have a nanostructure including a plurality of micro recess-protrusion structures on the surface of the substrate 1020 and a part where the metal thin film has been formed. The nanostructure on the surface of the substrate 1020 is formed by, for example, nanoimprinting or injection molding.

In addition, a molecule (linker) capable of appropriately securing a distance between the first specific-binding substance 114 and the base material 102a may be bound to the surface of the base material 102a from the viewpoint of easy immobilization of the first specific-binding substance 114 and from the viewpoint of orientation control and reactivity of the second specific-binding substance. The molecule that can serve as the linker is usually selected according to a charge characteristic of the surface of the base material. Examples of the molecule that can serve as the linker are a thiol derivative such as alkanethiol to form a self-assembled monolayer (SAM), a hydrophilic polymer including a polyethylene glycol chain (PEG chain), and an MPC polymer which is a polymer of MPC (2-methacryloyloxyethyl phosphorylcholine), which has a phospholipid polar group.

As shown in FIG. 3A, in the present embodiment, the base material 102a includes the substrate 1020 and an organic membrane 1022 disposed on the substrate 1020. The organic membrane 1022 is composed of the molecules that can serve as the linker described above. In this case, the first specific-binding substance 114 is immobilized on the surface of the base material 102a by binding the first specific-binding substance 114 to the organic membrane 1022. In addition, the first sugar molecule 116 is immobilized on the organic membrane 1022 by a chemical bond. As just described, the base material 102a includes the organic membrane 1022 on the substrate 1020, so that the first specific-binding substance 114 and the first sugar molecule 116 are stably immobilized on the surface of the base material 102a. The first sugar molecule 116 stably immobilized on the surface of the base material 102a is likely to remain without being separated from the surface, even when the sensor substrate 10a is washed. Since the hydroxy group (OH group) which the first sugar molecule 116 has acts in place of a water molecule, even when the sensor substrate 10a is dried, the deterioration of the first specific-binding substance 114 due to the drying is suppressed.

In the present embodiment, the organic membrane 1022 is a self-assembled monolayer (SAM). Examples of a single molecule included in SAM include a carboxyalkanethiol having approximately 4 to 20 carbon atoms, in particular, 10-carboxy-1-decanethiol. Since the SAM formed using a carboxyalkanethiol having approximately 4 to 20 carbon atoms has properties such as high transparency, low refractive index, and thin membrane thickness, there is little optical influence during the detection. One end of the SAM 1022 may be a functional group capable of binding to the surface of the substrate 1020. The one end of the SAM 1022 may be, for example, a thiol group. The other end of the SAM 1022 may be a functional group capable of binding to the first specific-binding substance 114 and the first sugar molecule 116. The other end of the SAM 1022 may be, for example, an amino group, a carboxyl group, or a biotin group. As just described, since the SAM 1022 has a reactive functional group at the terminal thereof, the first specific-binding substance 114 and the first sugar molecule 116 can easily form a chemical bond with the organic membrane 1022 (hereinafter, referred to as SAM 1022). As a result, the first specific-binding substance 114 and the first sugar molecule 116 are stably immobilized on the surface of the base material 102a.

In the sensor substrate 10a, the base material 102a is not particularly limited, as long as the first specific-binding substance 114 can be immobilized thereon and the first sugar molecule 116 can be immobilized thereon by the chemical bond. Another publically known base material may be used as the base material. In addition, a method for forming SAM is not specifically limited, a conventionally publically-known method may be used. A specific method will be described later.

The first specific-binding substance 114 is a substance capable of binding specifically to an analyte. Examples of the analyte include a protein, a lipid, a sugar, and a nucleic acid. Examples of the first specific-binding substance 114 include an antibody with respect to an antigen, an enzyme with respect to a substrate or a coenzyme, a receptor with respect to a hormone, a protein A or protein G with respect to an antibody, an avidin with respect to biotin, a calmodulin with respect to calcium, and a lectin with respect to sugar. If the analyte is a nucleic acid, a nucleic acid having a sequence capable of binding specifically to the nucleic acid may also be used as the first specific-binding substance 114.

As a method for immobilizing the first specific-binding substance 114 on the metal thin film, various appropriate methods may be used depending on the substance to be bound. For example, a modification group which is capable of generating a specific bond is introduced on the surface of the metal thin film, a functional group which corresponds to the modification group is introduced on the first specific-binding substance, and the modification group and the functional group are bound to each other. Thus, the first specific-binding substance 114 can be immobilized on the metal thin film.

For example, if the first specific-binding substance 114 is a protein such as an antibody, some of a plurality of amino acids which form the protein have a functional group such as a carboxyl group, an amino group, or a thiol group in the side chain thereof. The functional group and the base material 102a may be chemically bound, or the functional group may be modified with avidin, and then, the avidinized first specific-binding substance and the base material 102a may be chemically bound to each other.

In addition, in order to bind the first specific-binding substance 114 and the base material 102a more efficiently to each other, an activation treatment may be performed using a substance that promotes the binding reaction between the first specific-binding substance 114 and the base material 102a. The activation treatment method is, for example, a method comprising turning a carboxyl group of one of the SAM 1022 and the first specific-binding substance 114 into an activated ester using 1-(3-Dimethylaminopropyl)-3-ethylcarbodiimide hydrochloride (EDC) and N-Hydroxysuccinimide (NHS), and binding the carboxyl group of the activate ester to an amino group of the other of the first specific-binding substance 114 and the SAM 1022. In addition, the activation treatment method may be, for example, a method comprising binding the amino group of the SAM 1022 and the amino group of the first specific-binding substance 114 to each other using a substance having a plurality of aldehyde groups such as glutaraldehyde.

As the method for immobilizing the first specific-binding substance 114 on the base material 102a, other publically known methods may be used, as long as the first specific-binding substance 114 is not deactivated.

The first sugar molecule 116 is a sugar molecule having a carboxyl group or an amino group before the first sugar molecule 116 is immobilized on the surface of the base material 102a. Since the first sugar molecule 116 has a carboxyl group or an amino group in the molecule, the first sugar molecule 116 is immobilized on the surface of the base material 102a by a chemical bond. For example, in a case where the organic membrane 1022 is provided on the surface of the substrate 1020, the first sugar molecule 116 includes one of a carboxyl group and an amino group, the organic membrane 1022 includes the other of the carboxyl group and the amino group, and the chemical bond is formed by the reaction of the carboxyl group and the amino group. In this way, the first sugar molecule 116 is immobilized on the organic membrane 1022 by an amide bond that is a covalent bond. Covalent bonds have strong bonding strength among chemical bonds. As a result, the first sugar molecule 116 is stably immobilized on the surface of the base material 102a. The water-holding ability of the first sugar molecule 116 stably immobilized in this manner protects the surface of the sensor substrate 10a from drying and suppresses structural and functional deterioration of the first specific-binding substance 114. In this way, the storage stability of the sensor substrate 10a can be improved. As long as the first sugar molecule 116 is a sugar molecule having a carboxyl group or an amino group, the first sugar molecule 116 may be a monosaccharide, or may be a disaccharide or an oligosaccharide which is composed of 3 to 10 monosaccharides. The first sugar molecule 116 may be a polysaccharide (i.e., glycan) composed of 10 or more monosaccharides. Alternatively, the first sugar molecule 116 may have a plurality of functional groups in one molecule such as sialic acid. The first sugar molecule 116 may be a salt of these sugars.

Specifically, the first sugar molecule 116 may be, for example, an amino sugar having an amino group such as D-glucosamine, D-mannosamine, D-galactosamine, sialic acid, aminouronic acid, or muramic acid, or uronic acids having a carboxyl group such as D-glucuronic acid, D-mannuronic acid, L-guluronic acid, D-galacturonic acid, or L-iduronic acid, aldonic acids such as gluconic acid, a sugar acid having a carboxyl group such as ascorbic acid, a glucosaminoglycan (for example, hyaluronic acid) consisting of an amino sugar and an uronic acid, a polysaccharide having an amino group such as chitosan, a polysaccharide having a carboxyl group such as gum arabic, xanthan gum, gellan gum, or pectin or a salt thereof. As a method for immobilizing these first sugar molecules 116 on the surface of the base material 102a, a method similar to that for the first specific-binding substance 114 may be used. A specific method will be described later.

The first sugar molecule 116 is not particularly limited, as long as the first sugar molecule 116 is a sugar capable of being immobilized on the surface of the base material 102a by a chemical bond. As the first sugar molecule 116, a publically known sugar other than the sugars described above may be used.

The second sugar molecule 118 may be disposed at least on the surface of the first specific-binding substance 114, and may cover the entire surface of the base material 102a. In the present embodiment, as shown in FIG. 3B, the second sugar molecule 118 covers the entire surface of the base material 102a. In other words, the second sugar molecule 118 is disposed on the surface of the first specific-binding substance 114 and the first sugar molecule 116, both of which have been immobilized on the surface of the base material 102a. Furthermore, the second sugar molecule 118 is also disposed on a part where the first specific-binding substance 114 and the first sugar molecule 116 have not been immobilized on the surface of the base material 102a. The second sugar molecule 118 is disposed at least on the surface of the first specific-binding substance 114, so that the deterioration of the first specific-binding substance 114 due to drying is further suppressed. In addition, the second sugar molecule 118 covers the entire surface of the base material 102a, so that the second sugar molecule 118 is disposed not only on the surface of the first specific-binding substance 114 but also on the surface of the first sugar molecule 116. As a result, the deterioration of the first specific-binding substance 114 due to drying is further suppressed.

Unlike the first sugar molecule 116, the second sugar molecule 118 is not immobilized on the surface of the base material 102a by a chemical bond. The second sugar molecule 118 is disposed on the surface of the base material 102a by a weak force such as an intermolecular force (Van der Waals force). The second sugar molecule 118 may be the same kind of sugar as the first sugar molecule 116, or may be a different kind of sugar from the first sugar molecule 116. In other words, the second sugar molecule 118 may be a sugar molecule having a carboxyl group or an amino group, or may be a sugar molecule having no carboxyl group and no amino group. The first sugar molecule 116 and the second sugar molecule 118, which are different kinds of sugar molecules from each other, are disposed on the surface of the base material 102a, so that the effect of protecting the surface of the base material 102a from drying is improved. The second sugar molecule 118 may be a monosaccharide, a disaccharide, an oligosaccharide composed of 3 to 10 monosaccharides), or a polysaccharide (e.g., glycan) composed of 10 or more monosaccharides, or a salt of these sugars. If the second sugar molecule 118 is a sugar molecule which has a carboxyl group or an amino group, since the above description of the first sugar molecule 116 can be applied to the second sugar molecule 118, the description the second sugar molecule 118 is omitted. If the second sugar molecule 118 is a sugar molecule having no carboxyl group and no amino group, the second sugar molecule may be at least one of the following specific examples. For example, if the second sugar molecule 118 is a monosaccharide, tetrose (pentose) such as ribose, lyxose, xylose, arabinose, abiose, ribulose, or xylulose, hexose or cimarose (hexose) such as allose, talose, gulose, glucose, altrose, mannose, idose, galactose, psicose, fructose, sorbose or tagatose, or heptose (septacharose) such as sedoheptulose or coliose can be used. For example, if the second sugar molecule 118 is a disaccharide, trehalose, isotrehalose, cordobiose, sophorose, nigerose, lam inaribiose, maltose, cellobiose, isomaltose, gentibiose, lactose, sucrose, melibiose, palatinose, agarobiose, xylobiose, lactulose, or rutinose can be used. For example, if the second sugar molecule 118 is an oligosaccharide, a trisaccharide such as raffinose, gentianose, cellotriose, maltotriose, merentoose, a tetrasaccharide such as stachyose, an oligosaccharide such as xylooligosaccharide, isomaltoligosaccharide, gentiooligosaccharide, fructooligosaccharide, chitosan oligosaccharide, chitin oligosaccharide, or cellooligosaccharide can be used. For example, if the second sugar molecule 118 is a polysaccharide, curdlan, cyclodextrin, pectin, starch, agarose, amylose, amylopectin, arabinan, arabinogalactan, alginic acid, inulin, galactan, xylan, chitin, chitosan, glycogen, glucomannan, keratan sulfate, colominic acid, cellulose, dextran, pectin, pectic acid, heparan sulfate, heparin, mannan, lichenan, levan, or lentinan can be used.

Although not shown, the sensor substrate 10a according to the present embodiment may further include a blocking agent that covers at least a part of the surface of the base material 102a. The blocking agent is a substance capable of blocking a non-specific adsorption or blocking a non-specific binding (hereinafter, referred to as non-specific adsorption) of the contaminant in the sample and the second specific-binding substance labeled with a labeled substance to the surface of the sensor substrate 10a. An example of the contaminant includes proteins other than the analyte, lipids, sugars, peptides, or nucleic acids. The blocking agent may be, for example, skim milk, fish gelatin, bovine serum albumin (BSA), surfactant, casein, protamine, or polyethylene glycol. The blocking agent only needs to cover at least the region (namely, a gap region) where the first specific-binding substance 114 and the first sugar molecule 116 are not immobilized on the surface of the base material 102a, or covers the entire surface of the base material 102a. As a result, during the detection of the analyte, the non-specific adsorption on the surface of the base material 102a can be suppressed. In this way, noise generated by the non-specific adsorption (namely, non-specific adsorption noise) is suppressed, and the analyte can be detected accurately.

In addition, a blocking treatment means a process for blocking the above-mentioned non-specific adsorption. Using the blocking treatment, the influence on the detection of the analyte by non-specific adsorption can be suppressed. In the blocking treatment, the blocking agent may be added to the surface of the base material 102a after the first specific-binding substance 114 and the first sugar molecule 116 are immobilized on the surface of the base material 102a. More specifically, a blocking agent solution in which the blocking agent has been dissolved is prepared, and the blocking agent solution is added to the surface of the base material 102a of the sensor substrate 10a (at least to the surface of the region where the first specific-binding substance 114 and the first sugar molecule 116 have been immobilized). After the region is covered with the blocking agent solution for a predetermined time, the excess blocking agent solution is removed.

The second sugar molecule 118 may be mixed in the blocking agent solution and added to the surface of the base material 102a. A sugar solution including at least the second sugar molecule 118 may be prepared and applied to the surface of the base material 102a.

[Method for Manufacturing Sensor Substrate]

Figure 4A:
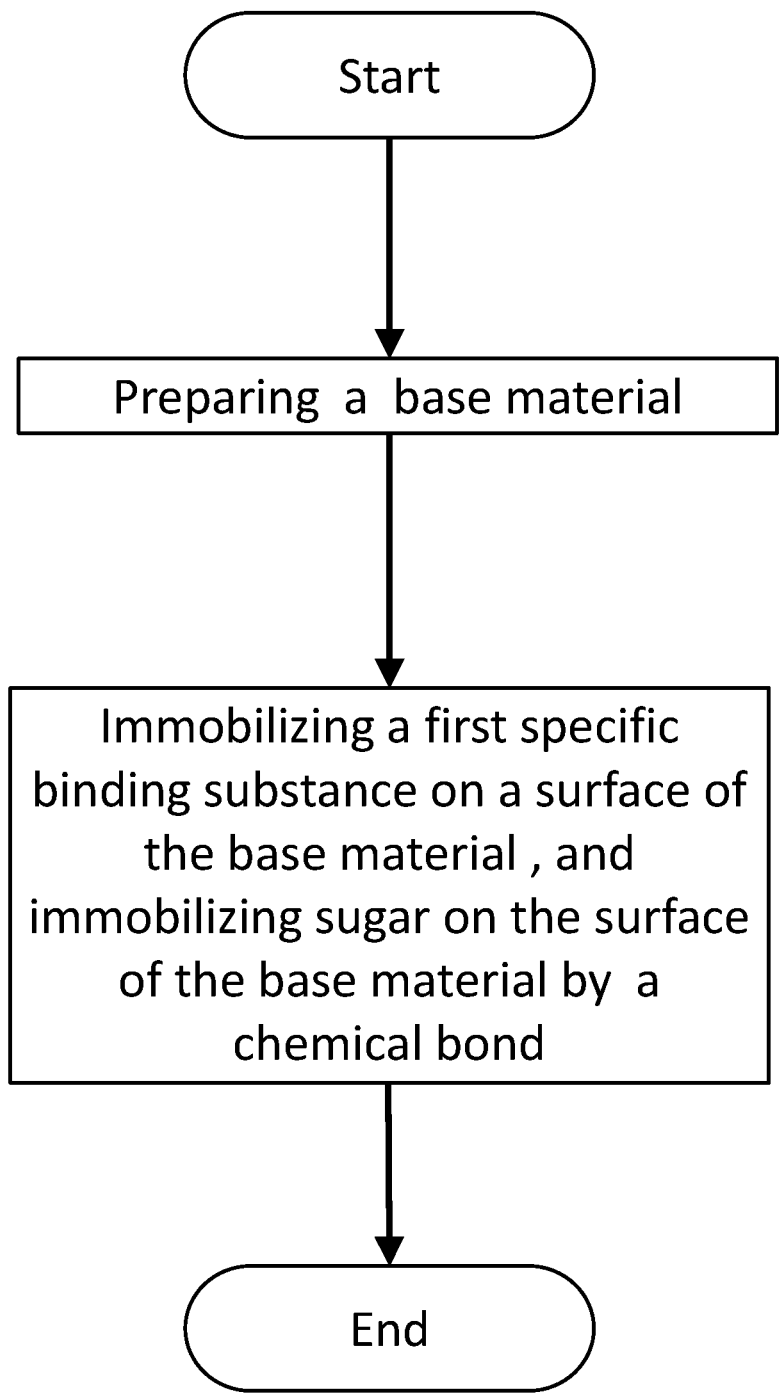
FIG. 4A is a flowchart showing one example of a method for manufacturing a sensor substrate according to the first embodiment.

FIG. 4A is a flowchart showing one example of a method for manufacturing the sensor substrate 10a according to the present embodiment. Hereinafter, the case where SAM is used as one example of the organic membrane will be described.

As shown in FIG. 4A, the method for manufacturing the sensor substrate 10a includes [1] a step S10 of preparing the base material 102a (hereinafter, referred to as the step S10) and [2] a step S20 of immobilizing the first specific-binding substance 114 capable of binding specifically to an analyte on the surface of the base material 102a, and immobilizing the first sugar molecule 116 by a chemical bond to the surface of the base material 102a (hereinafter, referred to as the step S20).

Figure 4B:
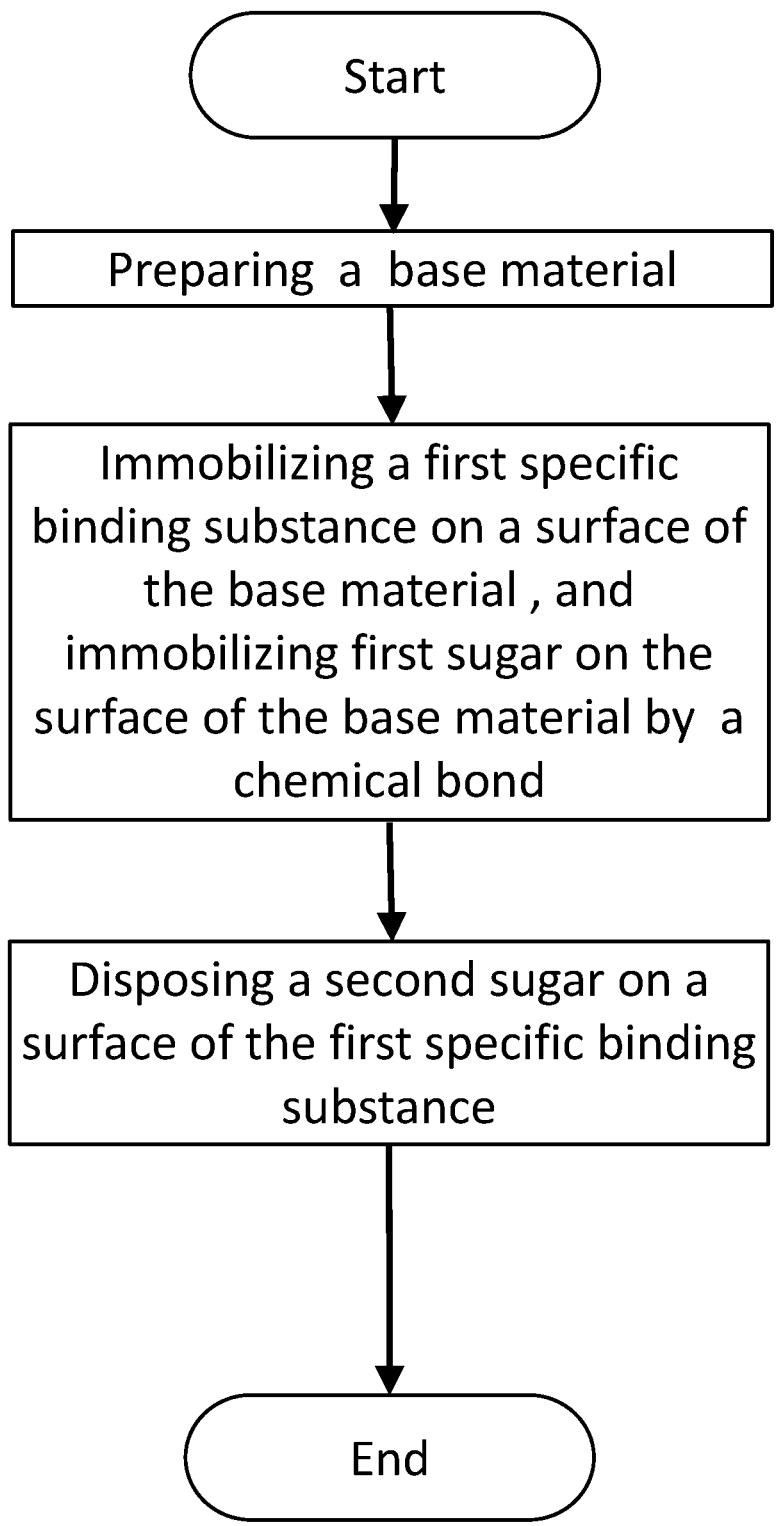
FIG. 4B is a flowchart showing another example of the method for manufacturing the sensor substrate according to the first embodiment.

FIG. 4B is a flowchart showing another example of the method for manufacturing the sensor substrate 10a according to the present embodiment.

As shown in FIG. 4B, the method for manufacturing the sensor substrate 10a may include [1] the step S10 of preparing the base material 102a, [2] the step S20 of immobilizing the first specific-binding substance 114 capable of binding specifically to an analyte on the surface of the base material 102a, and disposing the first sugar molecule 116 on the surface of the base material 102a, and [3] a step S30 of disposing the second sugar molecule 118 at least on the surface of the first specific-binding substance 114 (hereinafter, referred to as the step S30).

Hereinafter, the method for manufacturing the sensor substrate 10a will be described more specifically. FIGS. 5 to 9 are diagrams schematically illustrating one example of the method for manufacturing the sensor substrate 10a according to the present embodiment. FIGS. 5 to 9 are schematic cross-sectional views showing a part of the sensor substrate 10a (here, a part where the detection region 110a is formed).

[1] If the sensor substrate 10a is used as a plasmon excitation sensor, the step S10 includes, for example, the following three steps (S11, S12, and S13). The step S11 is a step of preparing the substrate 1020. The step S12 is a step of forming a metal thin film on the surface of the substrate 1020. The step S13 is a step of forming an organic membrane 1022 (hereinafter, SAM 1022) on the metal thin film.

Hereinafter, each step will be described more specifically. Illustration of the steps S11 and S12 are omitted.

[1-1] In the step S11, for example, if the material of the substrate 1020 is a resin material, the substrate 1020 is formed by injection molding. In this case, the surface of the substrate 1020 may be smooth or may have a nanostructure consisting of a plurality of micro recess-protrusion structures. The nanostructure may be formed on the surface of the smooth substrate 1020 by nanoimprinting.

[1-2] Subsequently, in the step S12, a metal thin film (not shown) is formed on the surface of the substrate 1020 provided in the step S11. The material of the metal thin film is, for example, a metal including at least one kind of metal such as gold, silver, aluminum, copper, and platinum, or an alloy thereof. The method for forming the metal thin film is not particularly limited. The metal thin film is formed on the surface of the substrate 1020, for example, by a vacuum membrane forming method such as an electron beam heating vacuum deposition method, a resistance heating vacuum deposition method, a magnetron sputtering method, a plasma assisted sputtering method, an ion assisted deposition method, or an ion plating method.

Figure 5:
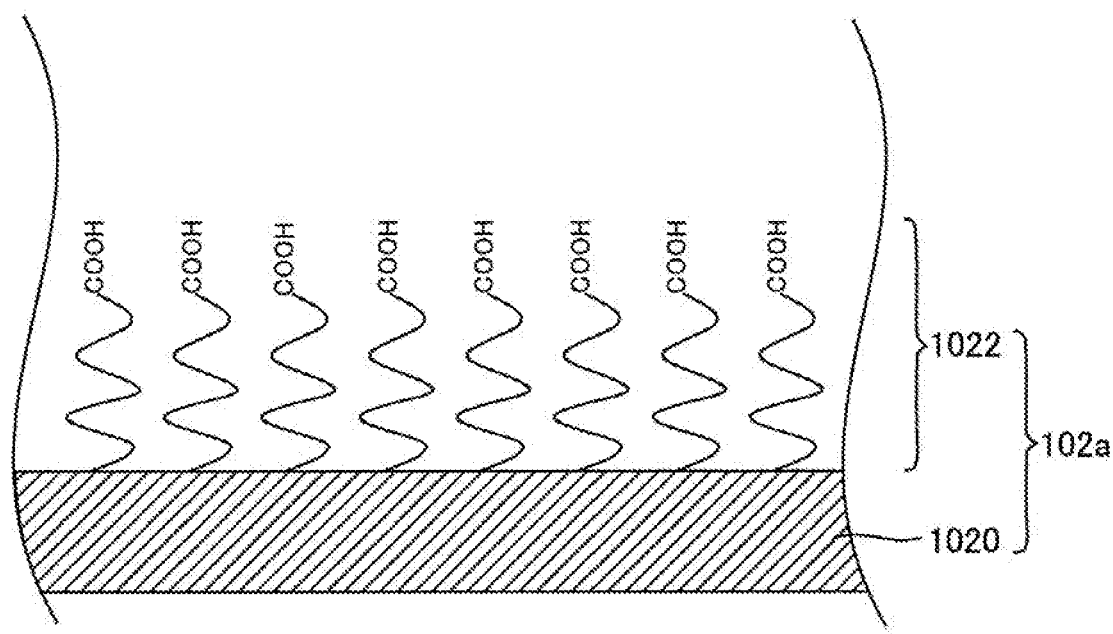
FIG. 5 is a schematic diagram for illustrating one example of the method for manufacturing the sensor substrate according to the first embodiment.

[1-3] Subsequently, in the step S13, as shown in FIG. 5, the SAM 1022 is formed on one of principal surfaces of the substrate 1020 (here, the surface on which the nanostructure and the metal thin film have been formed). The method for forming the SAM is not particularly limited, and a commonly used method may be used. For example, a method in which a substrate having a metal thin film formed on its surface and a layer formed of a mask material formed on the surface of the thin membrane is immersed in an ethanol solution including a carboxyalkanethiol having approximately 4 to 20 carbon atoms (for example, 10-carboxy-1-decanethiol) may be employed. In this method, a thiol group terminal of 10-carboxy-1-decanethiol (hereinafter, referred to as a single molecule) is bound to a metal, so that the single molecules are immobilized on the surface of the metal thin film, and the immobilized single molecules are aggregated on the surface of the metal thin film. In this way, a self-assembled monolayer (namely, the SAM) is formed.

As described above, the base material 102a in which the SAM 1022 has been arranged on the surface of the substrate 1020 is provided.

[2] The step 20 includes the following four steps (S21, S22, S23, and S24). The step S21 is a step of activating a reactive functional group of the polymer that forms the organic membrane 1022. The step S22 is a step of adding the first specific-binding substance 114 and the first sugar molecule 116 to the surface of the base material 102a. The step S23 is a step of immobilizing the added first specific-binding substance 114 and the added first sugar molecule 116 to the SAM 1022 by chemical bond. The step S24 is a step of removing the excess first specific-binding substance 114 and the excess first sugar molecule 116 that have not been immobilized on the SAM 1022.

Hereinafter, each step will be described more specifically. Note that illustration of the step S21 is omitted.

[2-1] In the step S21, the reactive functional group (for example, a carboxyl group) of the SAM 1022 is activated to be turned into a form which easily reacts with the reactive functional groups (for example, amino groups) of the first specific-binding substance 114 and the first sugar molecule 116. In the step S21, for example, the carboxyl group of the single molecule (for example, 10-carboxy-1-decanethiol) forming the SAM 1022 is turned into an activated ester with water-soluble carbodiimide (WSC) and N-hydroxysuccinimide (NHS).

Figure 6:
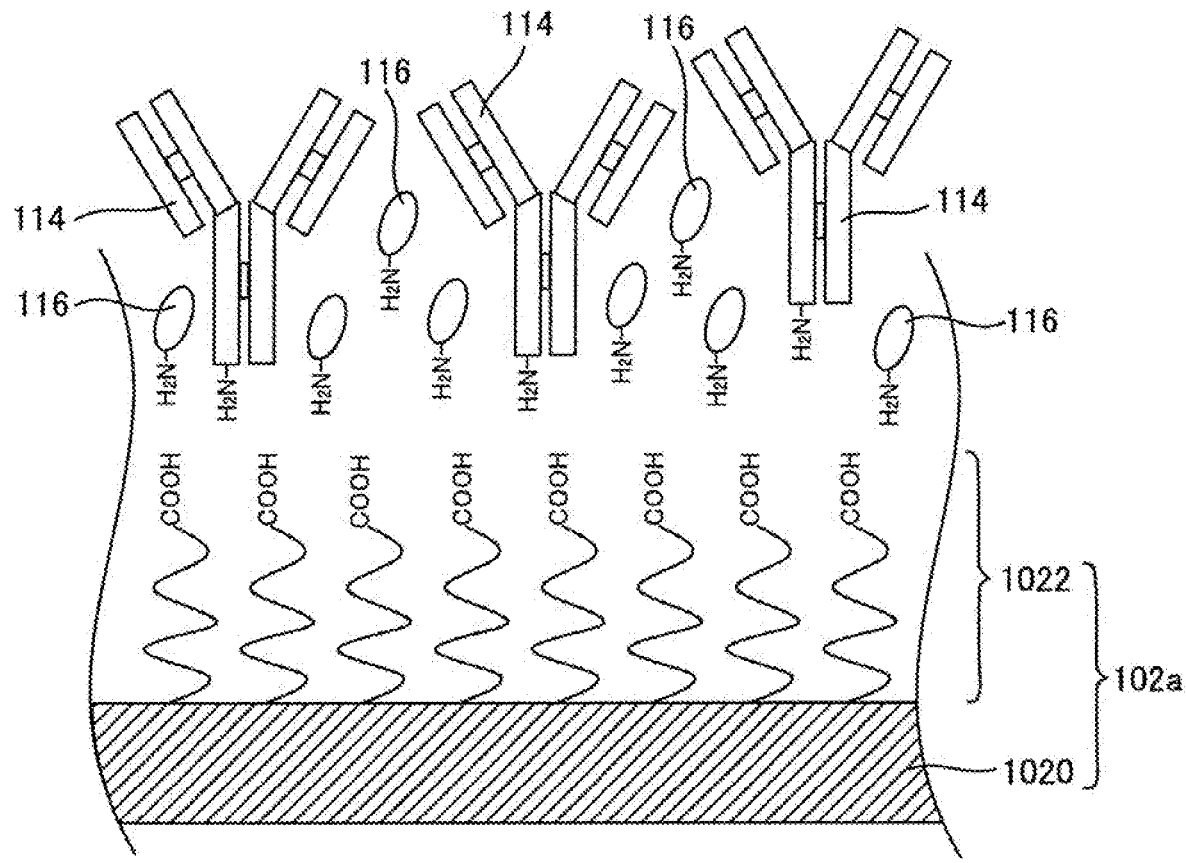
FIG. 6 is a schematic diagram for illustrating one example of the method for manufacturing the sensor substrate according to the first embodiment.

[2-2] Next, as shown in FIG. 6, in the step S22, a solution including the first specific-binding substance 114 and the first sugar molecule 116 is added onto the SAM 1022 in which the reactive functional group has been activated in the step S21.

Figure 7:
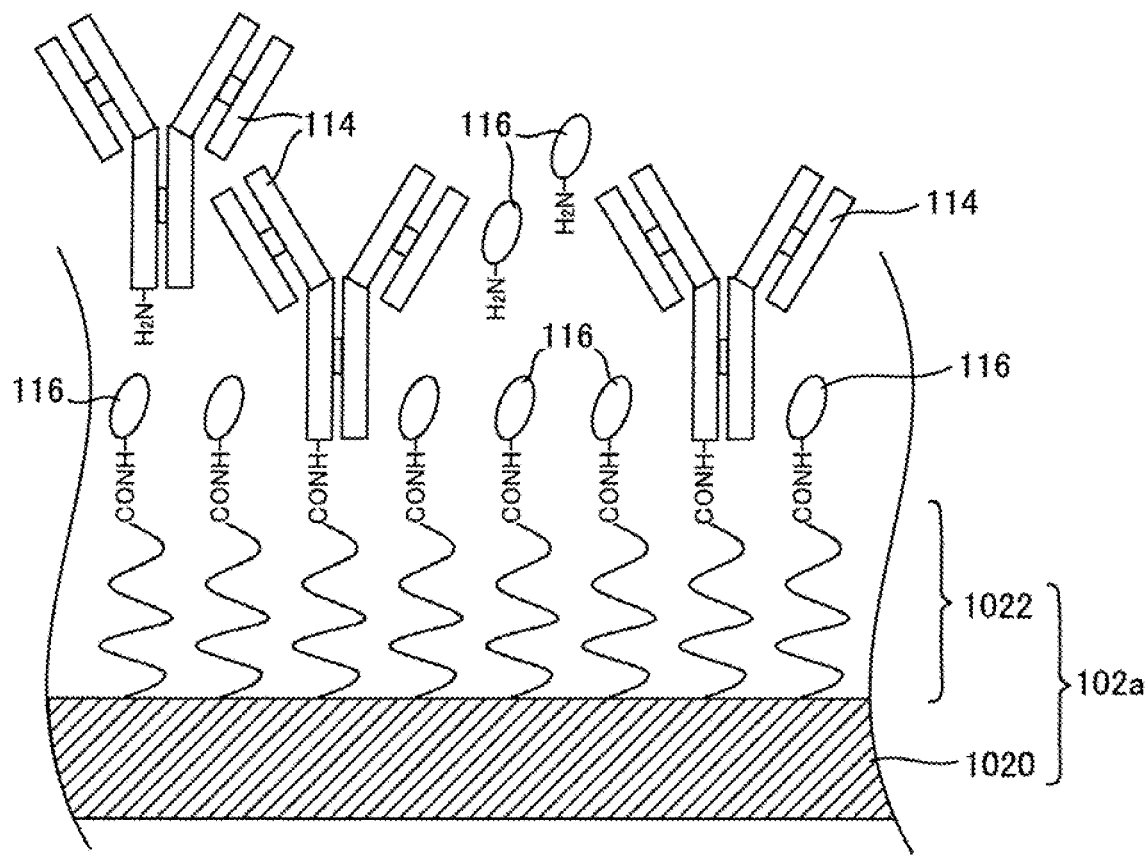
FIG. 7 is a schematic diagram for illustrating one example of the method for manufacturing the sensor substrate according to the first embodiment.

[2-3] Then, as shown in FIG. 7, in the step S23, a dehydration reaction between the carboxyl group of the activated ester of the SAM 1022 and the amino groups of the first specific-binding substance 114 and the first sugar molecule 116 is caused to occur. In this way, the first specific-binding substance 114 and the first sugar molecule 116 are immobilized on the SAM 1022. In this case, the first specific-binding substance 114 and the first sugar molecule 116 are immobilized on the SAM 1022 by peptide bonds.

Figure 8:
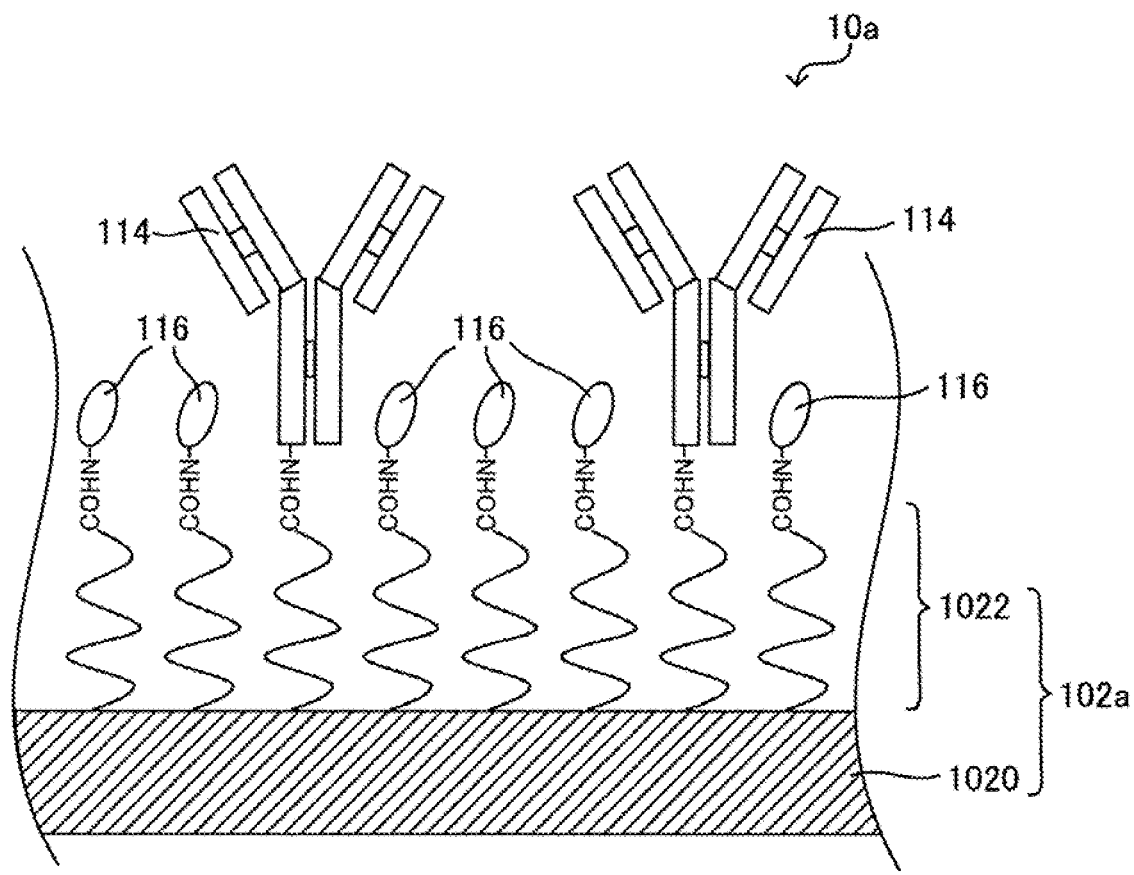
FIG. 8 is a schematic diagram for illustrating one example of the method for manufacturing the sensor substrate according to the first embodiment.
Figure 9:
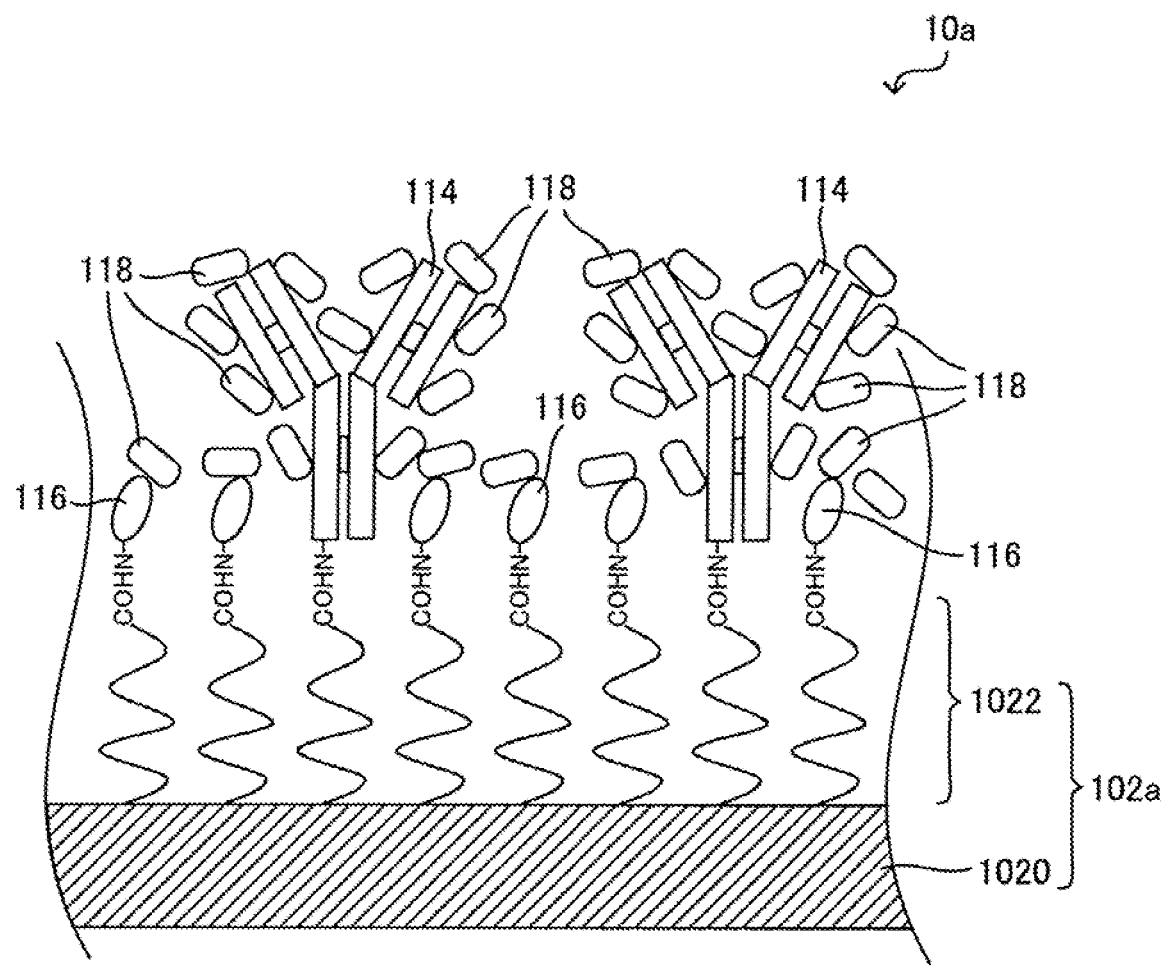
FIG. 9 is a schematic diagram for illustrating one example of the method for manufacturing the sensor substrate according to the first embodiment.

[2-4] Next, as shown in FIG. 8, in the step S24, the excess first specific-binding substance 114 and the excess first sugar molecule 116 that have not been immobilized on the SAM 1022 are washed and removed with a phosphate buffered saline (PBS). In this way, the sensor substrate 10a in which the first specific-binding substance 114 has been immobilized on the surface of the base material 102a and the first sugar molecule 116 has been immobilized on the surface of the base material 102a by chemical bond can be provided.

[3] In the step S30, the second sugar molecule 118 is disposed at least on the surface of the first specific-binding substance 114. Here, the blocking agent and the second sugar molecule 118 are added onto the SAM 1022 in a blocking treatment step. In the blocking treatment step, preformed is a treatment for blocking the non-specific adsorption or blocking the non-specific binding, to the surface of the base material 102a, of the contaminant in the sample (for example, proteins other than the analyte, a lipid, sugar, a peptide, or a nucleic acid) and the second specific-binding substance labeled with the labeled substance on the detection region 110a of the sensor substrate 10a. Specifically, in the step S30, a sugar-containing blocking agent solution including the blocking agent and the second sugar molecule 118 is prepared, and the sugar-containing blocking agent solution is added onto the SAM 1022. In the step S30, the sugar solution including the second sugar molecule 118 may be added onto the SAM 1022 after the blocking treatment step. In this way, the sensor substrate 10a in which the second sugar molecule 118 has been disposed at least on the surface of the first specific-binding substance 114 can be provided.

[Method of Detecting Analyte]

Figure 10A:
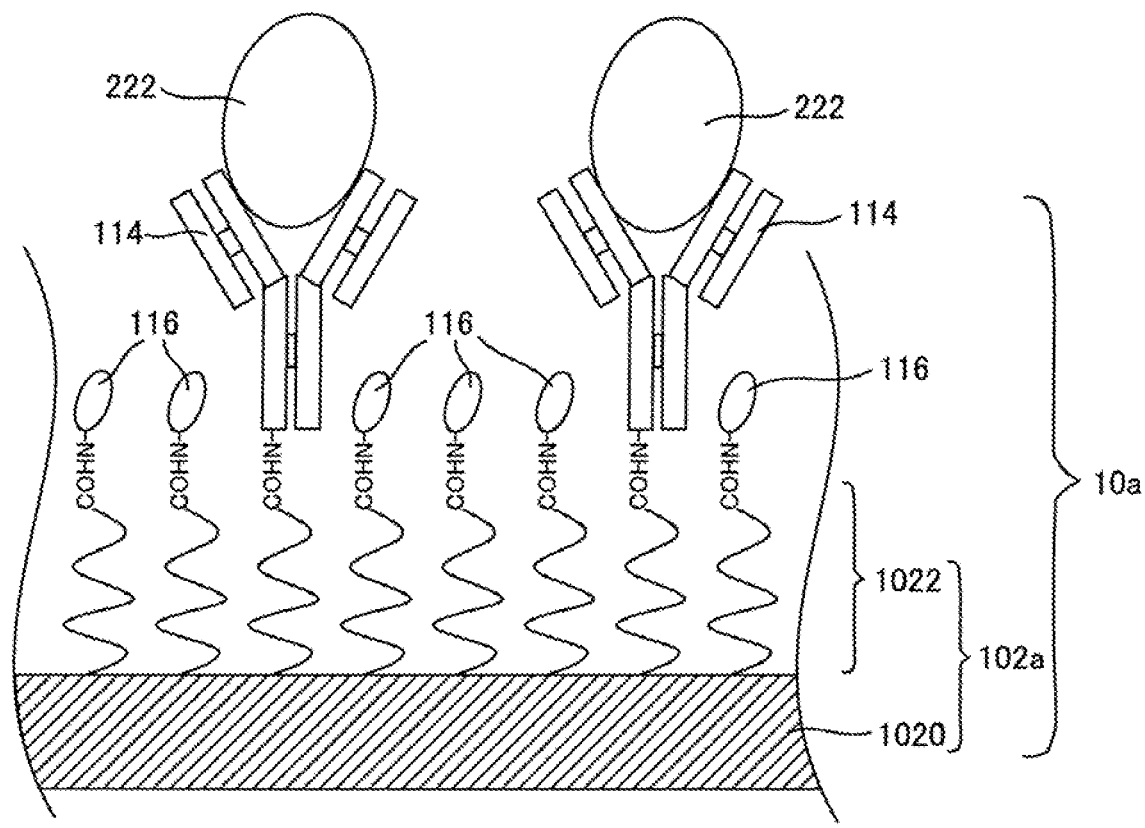
FIG. 10A is a diagram for schematically illustrating one example of a method of detecting an analyte in the first embodiment.
Figure 10B:
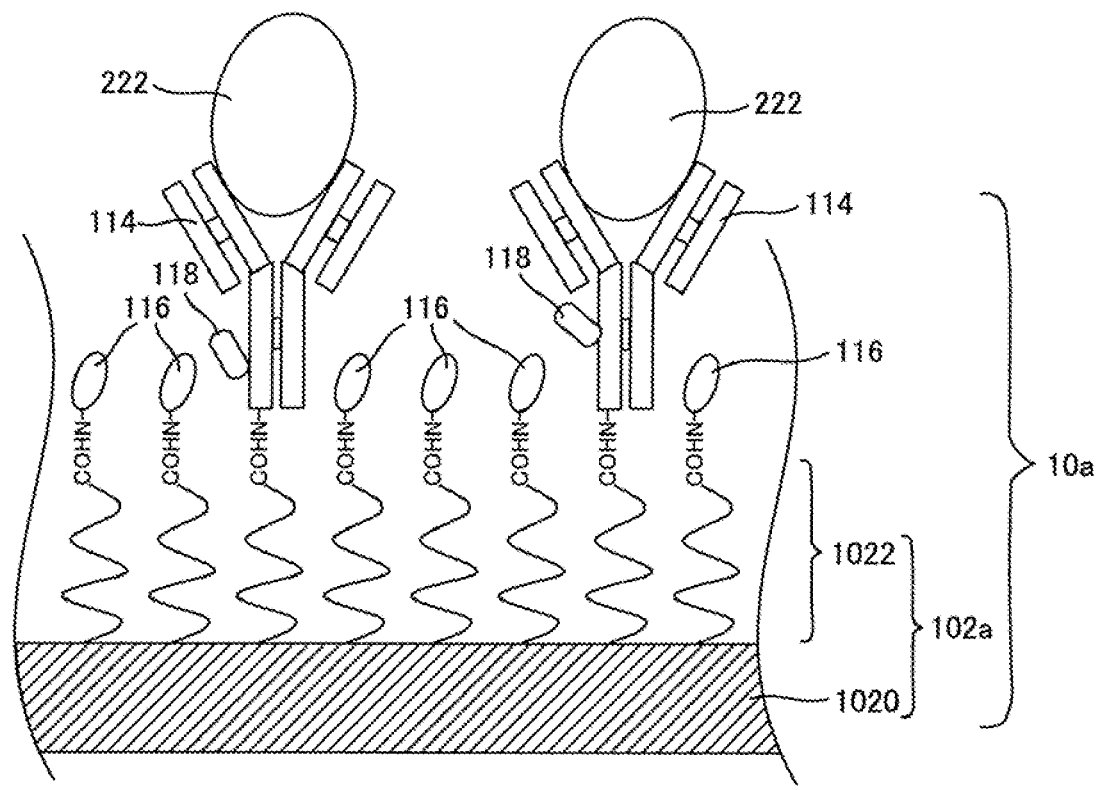
FIG. 10B is a diagram for schematically illustrating another example of the method of detecting the analyte in the first embodiment.
Figure 11A:
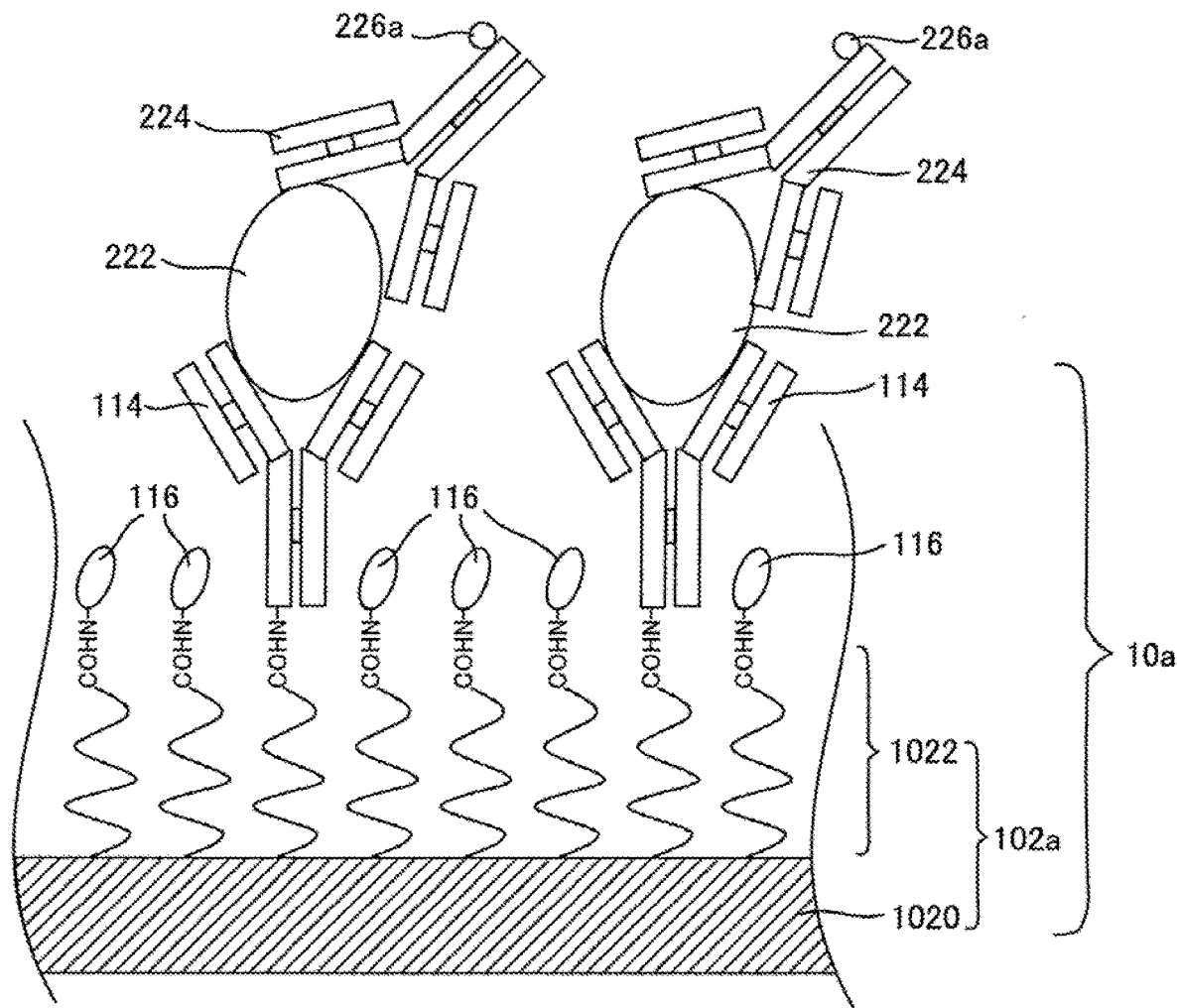
FIG. 11A is a diagram for schematically illustrating one example of the method of detecting the analyte in the first embodiment.
Figure 11B:
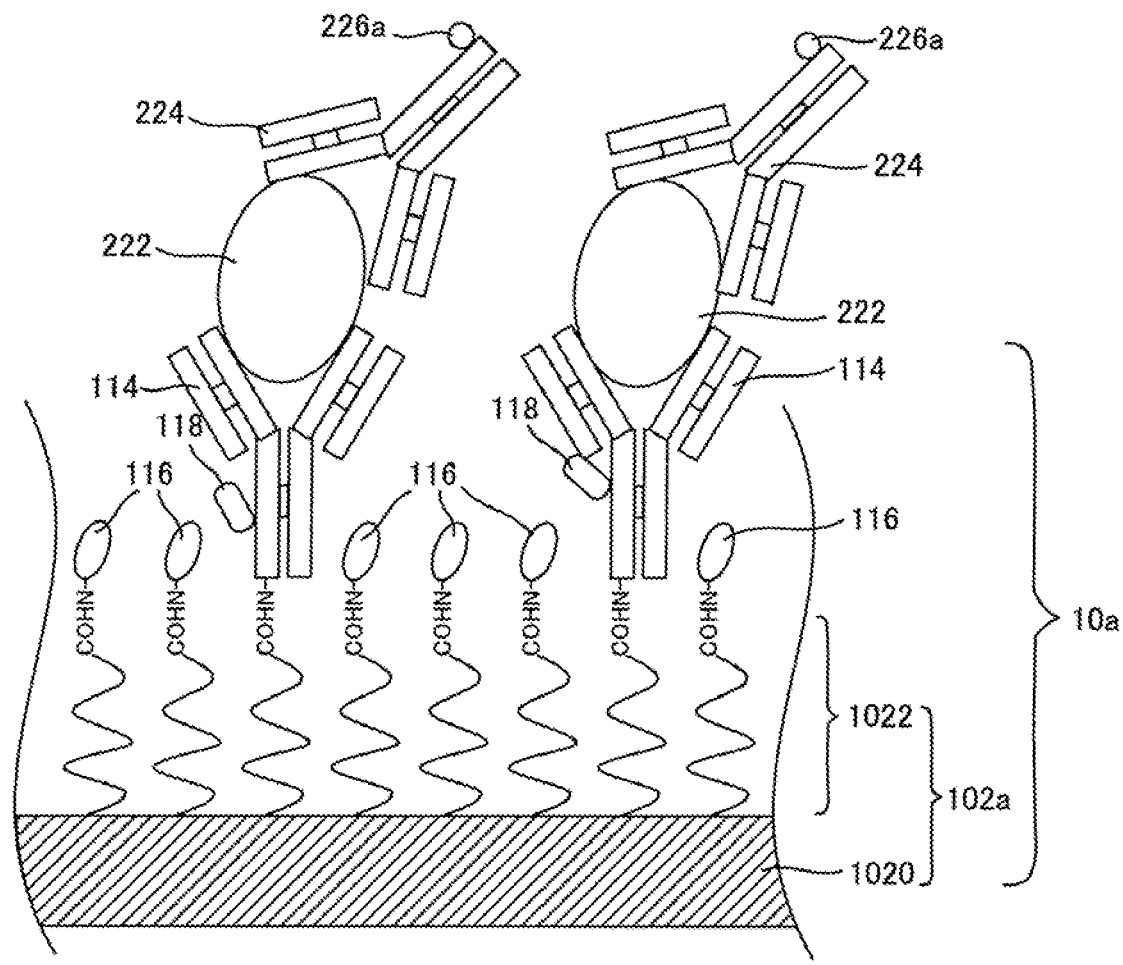
FIG. 11B is a diagram for schematically illustrating another example of the method of detecting the analyte in the first embodiment.

Next, a method of detecting an analyte using the detection device 100a according to the present embodiment will be described with reference to FIGS. 10A to 11B. FIG. 10A and FIG. 11A are diagrams for schematically illustrating one example of a method of detecting an analyte 222 in the present embodiment. FIGS. 10B and 11B are diagrams for schematically illustrating another example of the method of detecting the analyte 222 in the present embodiment.

As shown in FIG. 10A or FIG. 10B, a sample that may include the analyte 222 is added onto the sensor substrate 10a. As a result, the analyte 222 binds specifically to the first specific-binding substance 114 immobilized on the base material 102a of the sensor substrate 10a.

Next, as shown in FIG. 11A or 11B, a second specific-binding substance 224 labeled with a labeled substance 226a is added onto the sensor substrate 10a. The second specific-binding substance 224 has a property of binding specifically to the analyte 222. As a result, a composite which is a sandwich structure in which the first specific-binding substance 114, the analyte 222, and the second specific-binding substance 224 labeled with the labeled substance 226a have been sequentially bound is formed on the surface of the sensor substrate 10a.

Next, the surface of the sensor substrate 10a is washed with a buffer solution to remove the excess second specific-binding substance 224 and the contaminant which is included in the sample.

The labeled substance 226a is, for example, a fluorescent substance. In this case, the analyte 222 is detected by irradiating the detection region 110a of the sensor substrate 10a with the excitation light from the light source 30a and detecting the intensity of the fluorescence emitted from the fluorescent substance.

Second Embodiment

[Configuration of Detection Device]

Figure 12:
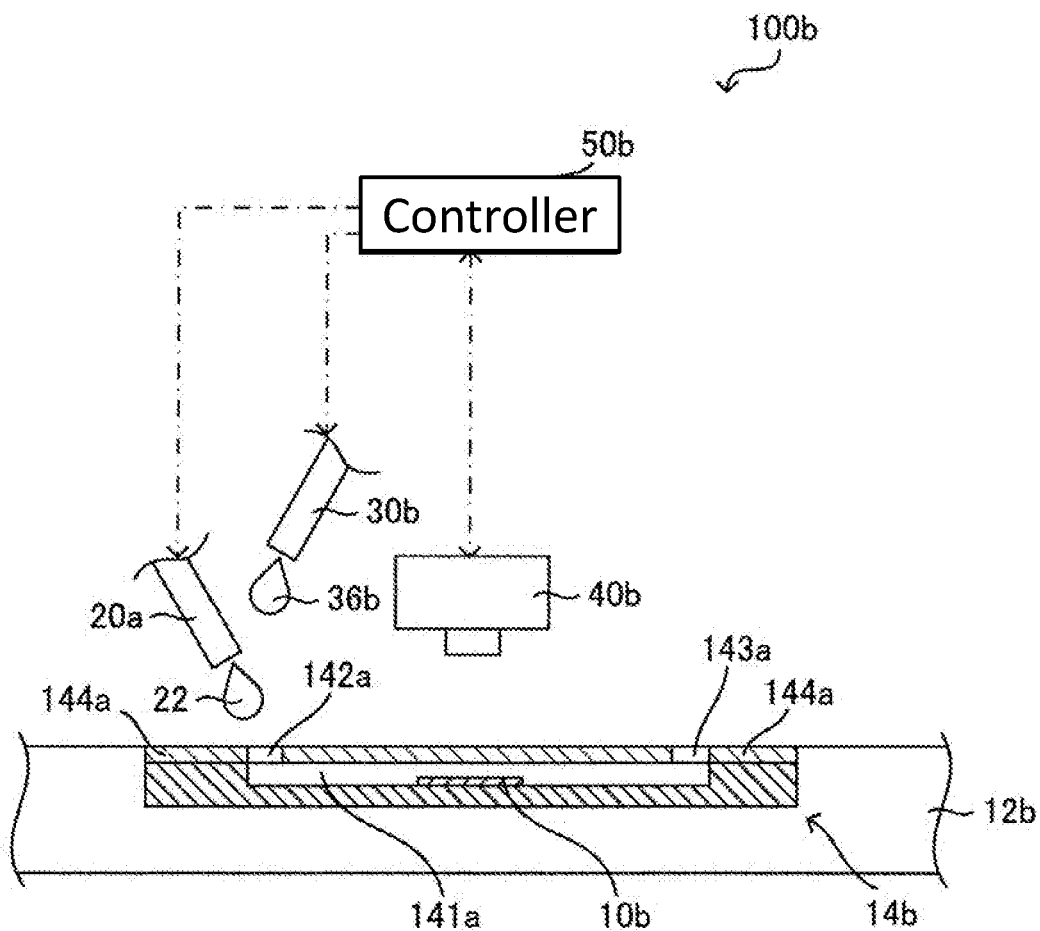
FIG. 12 is a schematic configuration diagram showing one example of a detection device according to a second embodiment.

FIG. 12 is a schematic configuration diagram illustrating one example of a detection device 100b according to the present embodiment.

As illustrated in FIG. 12, the detection device 100b comprises the sensor substrate 10b, the introduction part 20a, an application part 30b (here, a second introduction part 30b), a detection part 40b, and a controller 50b. In the present embodiment, the detection device 100b comprises a sensor device 12b. The sensor device 12b comprises a sensor cell 14b including the sensor substrate 10b.

Hereinafter, the configuration of the detection device 100b will be described. In addition, the same reference signs are assigned to the same elements as those of the first embodiment, and the description thereof is omitted. Here, only differences from the detection device 100a according to the first embodiment will be described.

The detection device 100b according to the present embodiment is a device for optically detecting the amount of an analyte. The present embodiment is different from the detection system of the first embodiment in that a signal of a dye or chemiluminescence generated due to a chemical reaction between substances is detected.

The second introduction part 30b is one example of the application part 30b. The application part 30b applies an inducer capable of inducing a signal from the labeled substance to the sensor substrate 10b into which the second specific-binding substance labeled with the labeled substance and the sample have been introduced. For example, the labeled substance is an enzyme. The inducer is, for example, a substrate or a mixture of a substrate and an indicator. The substrate may be a substance capable of developing color by being decomposed by an enzyme, or may be a substance that does not develop color. In the case where the substrate is a substance that does not develop color due to decomposition by an enzyme, it is desirable that the inducer is a mixture of a substrate and an indicator. The indicator is, for example, a pH indicator or an indicator capable of generating a coloring substance by reacting with a substrate generated due to the decomposition of the substrate (hereinafter, a decomposition product).

As shown in FIG. 12, the detection part 40b is, for example, a CCD camera. In the present embodiment, the development of color of the detection region 110a (see FIG. 2) of the sensor substrate 10b can be observed with the CCD camera to detect the analyte 222 visually.

[Method of Detecting Analyte]

Figure 13A:
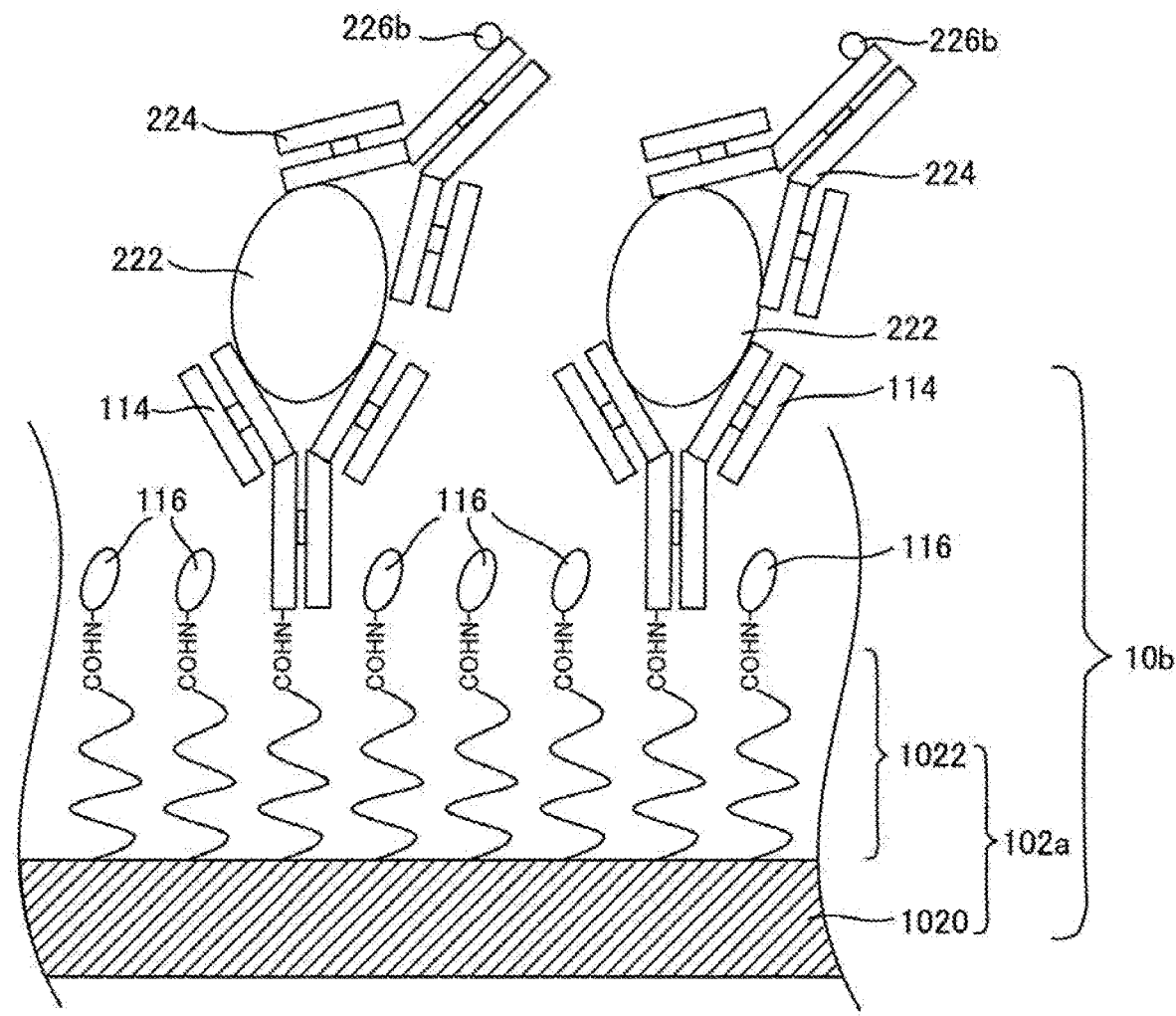
FIG. 13A is a schematic diagram for illustrating one example of a method of detecting an analyte in the second embodiment.
Figure 13B:
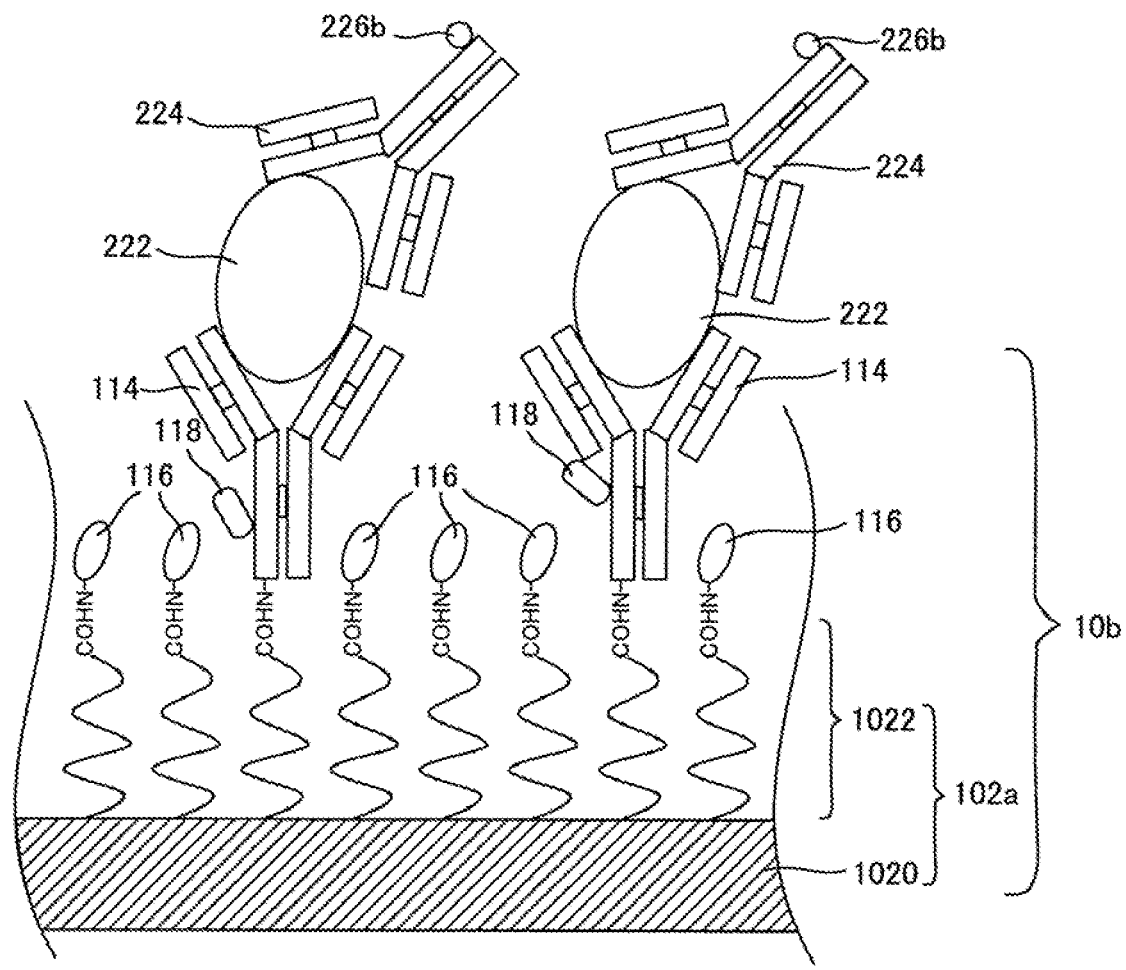
FIG. 13B is a schematic diagram for illustrating another example of the method of detecting the analyte in the second embodiment.
Figure 14A:
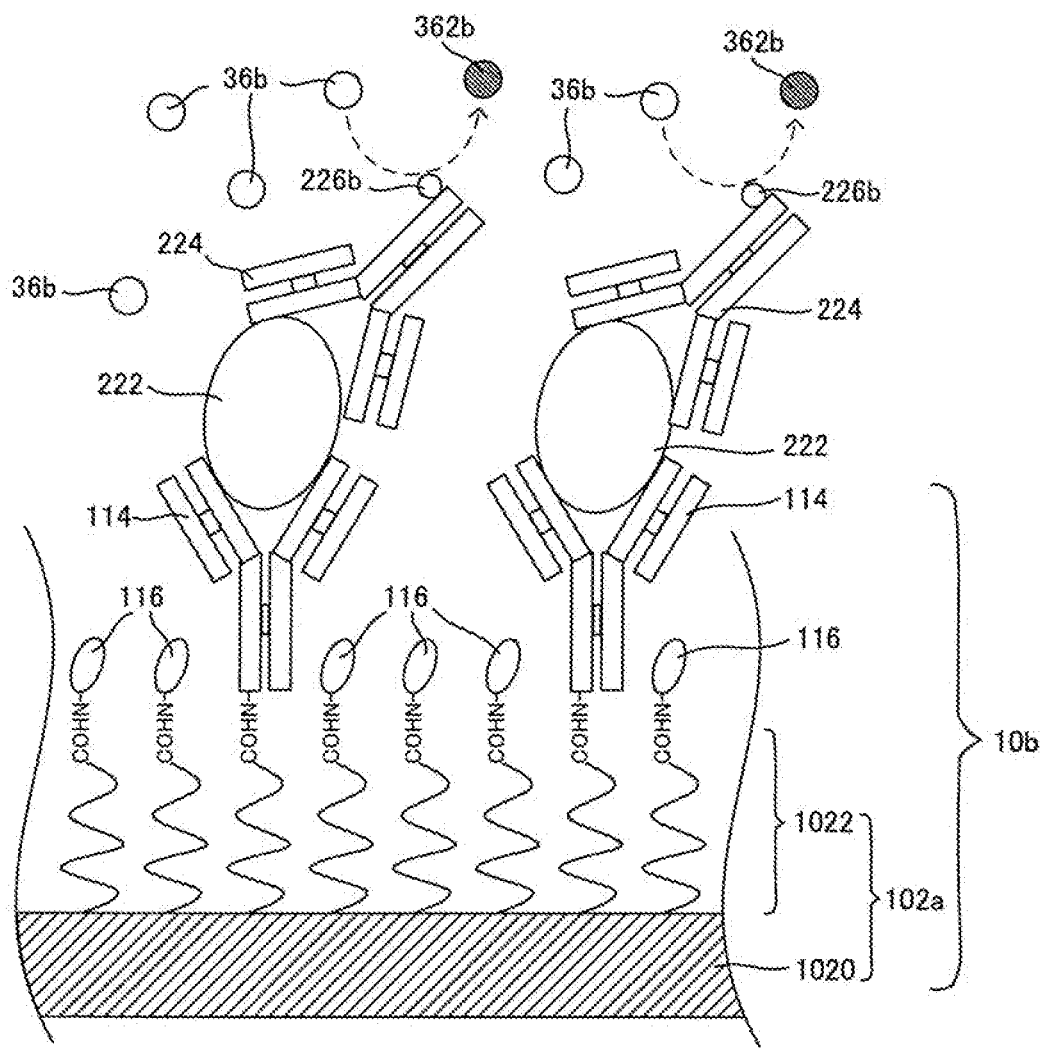
FIG. 14A is a schematic diagram for illustrating one example of the method of detecting the analyte in the second embodiment.
Figure 14B:
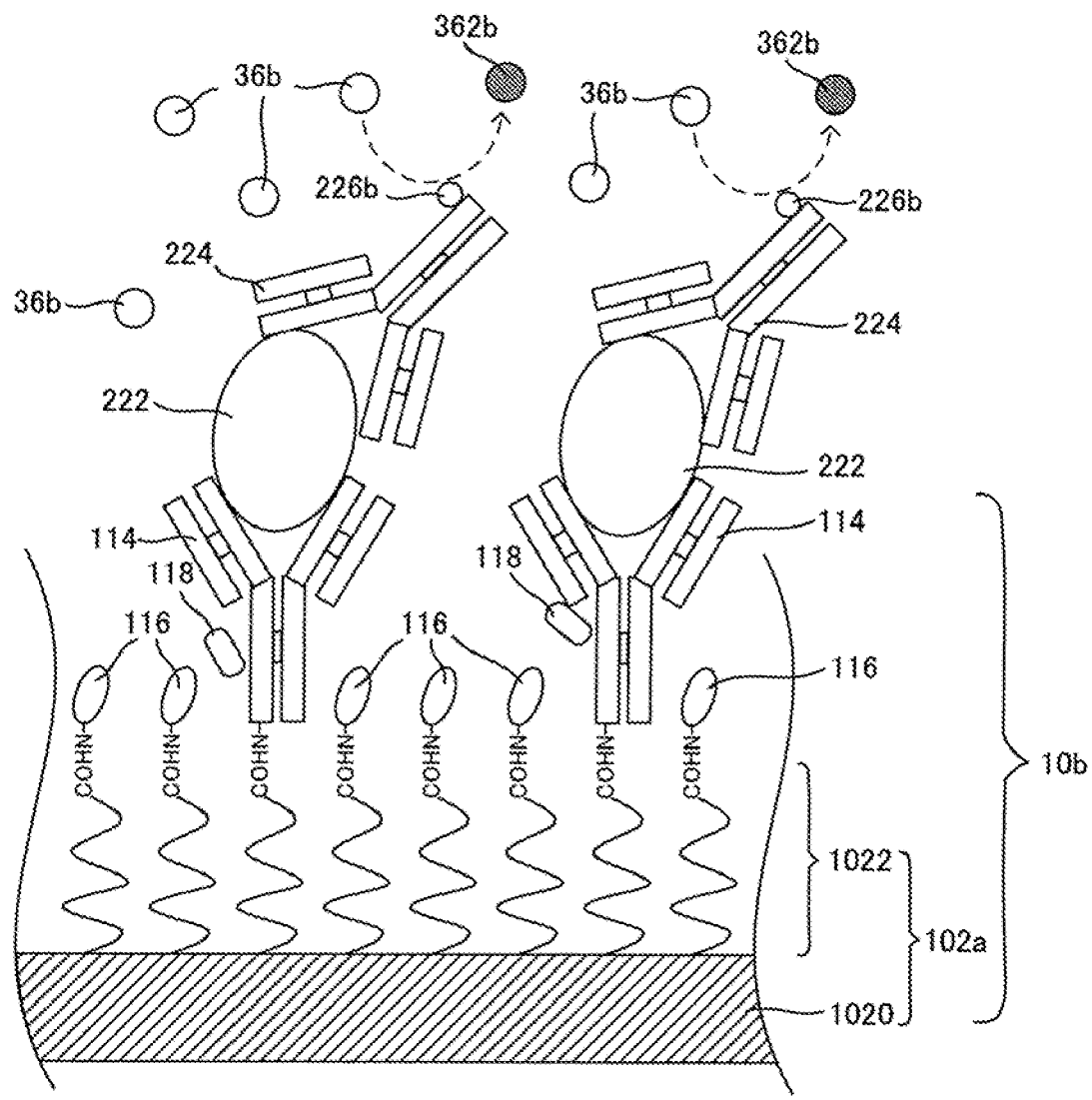
FIG. 14B is a schematic diagram for illustrating another example of the method of detecting the analyte in the second embodiment.

Next, a method of detecting the analyte with the detection device 100b according to the present embodiment will be described with reference to FIGS. 13A to 14B. FIG. 13A and FIG. 14A are diagrams for schematically illustrating one example of a method of detecting the analyte 222 in the present embodiment. FIGS. 13B and 14B are diagrams for schematically illustrating another example of the method of detecting the analyte 222 in the present embodiment.

A sample that may include the analyte 222 is added onto the sensor substrate 10b. As a result, the analyte 222 binds specifically to the first specific-binding substance 114 immobilized on the base material 102a of the sensor substrate 10b.

Next, as shown in FIG. 13A or FIG. 13B, the second specific-binding substance 224 labeled with a labeled substance 226b is added onto the sensor substrate 10b. The second specific-binding substance 224 binds specifically to the analyte 222. As a result, a composite which is a sandwich structure in which the first specific-binding substance 114, the analyte 222, and the second specific-binding substance 224 labeled with the labeled substance 226b are sequentially bound is formed on the surface of the sensor substrate 10b.

Next, the surface of the sensor substrate 10b is washed with a buffer solution to remove the excess second specific-binding substance 224 and the contaminant included in the sample. As described above, the labeled substance 226b is an enzyme.

Next, as shown in FIG. 14A or FIG. 14B, an inducer 36b (here, a substrate 36b) is introduced from the second introduction part 30b onto the sensor substrate 10b. In the detection region 110a of the sensor substrate 10b, the introduced substrate 36b is decomposed with the labeled substance 226b. Here, the substrate 36b is decomposed with the enzyme to be turned into a coloring substance 362b. The color emitted by the coloring substance 362b is detected with the CCD camera to detect the analyte 222.

In the present embodiment, the example in which the substrate 36b is decomposed to be turned into the coloring substance 362b has been described. However, depending on the decomposition product, there is a possibility that the color is not developed as it is. The decomposition products that are the coloring substances 362b include, for example, a decomposition product capable of emitting fluorescence when irradiated with light of a predetermined wavelength such as UV, and a decomposition product capable of developing color by reacting with an indicator which is further added.

Note that electrochemical detection may be used as the detection method. For example, an enzyme and a substrate that generate an electrochemically active substance by an enzyme substrate reaction are selected, the second specific-binding substance is labeled with the enzyme to form a composite which is a sandwich structure, and then, the substrate is added. Subsequently, the electrochemically active substance generated due to the enzyme substrate reaction is detected with the detection electrode, and the amount of the analyte is calculated from the current value. Here, the enzyme is not particularly limited, and ALP (Alkaline Phosphatase) or glucose oxidase may be used, and the substrate may be pAPP (p-Aminophenyl Phosphate) or potassium ferricyanide for each enzyme. The electrochemically active substance produced due to the enzyme substrate reaction is, for example, pAP (paraaminophenol), potassium ferrocyanide, ferrocene or a ferrocene derivative.

EXAMPLES

Hereinafter, the sensor substrate of the present disclosure will be described concretely in the examples. Note that the present disclosure is not limited to the following example at all.

Inventive Example 1

A sensor substrate according to the inventive example 1 was produced by the following method.

[1] Production of Sensor Substrate

[1-a] Step of Preparing Base Material

A resin film formed of polyolefin having a thickness of 188 μm was used as a substrate. This resin film has a plurality of micro recess-protrusion structures (hereinafter, referred to as nanostructures) formed by nanoimprinting on the surface thereof. A gold thin membrane was formed on the surface of the nanostructure by a sputtering method. The thickness of the gold thin membrane was 300 to 500 nm. In this way, the substrate having a metal nanostructure on the surface thereof was provided.

Next, the substrate having the metal nanostructure was immersed in an ethanol solution including hydroxy-EG3-undecanthiol and carboxy-EG6-undecanthiol for not less than 24 hours. In this way, an organic membrane (here, SAM) was formed on the surface of the gold thin membrane. The substrate after the immersion was taken out from the ethanol solution, washed with ethanol and ultrapure water, and then, dried with an air gun. In this way, the base material in which SAM was formed on the surface of the substrate was provided.

[1-b] Step of Immobilizing First Specific-Binding Substance and First Sugar Molecule on Surface of Base Material In the inventive example 1, a first VHH antibody was used as the first specific-binding substance. An antigen of the first VHH antibody used in the inventive example 1 was a nucleoprotein (hereinafter, sometimes referred to as "NP")

of an influenza virus. In addition, as the first sugar molecule, D(+)-glucosamine hydrochloride (hereinafter, referred to as glucosamine) was used.

A MES (2-morpholinoethanesulfonic acid) buffered physiological saline (0.5 mL) including 100 mM of N-Hydroxysuccinimide (i.e., NHS) and 400 mM of (1-(3-Dimethylaminopropyl)-3-ethylcarbodiimide hydrochloride) (i.e., EDC) was dropped on the surface of the substrate provided in the above step [1-a] to react. To this was added 10 μg/mL of the first VHH antibody and 0.5 mL of a phosphate buffered saline (PBS) solution including 1% (w/v) D(+)-glucosamine hydrochloride to react. As a result, the first VHH antibody and glucosamine were immobilized on the SAM. Subsequently, the first VHH antibody and glucosamine were washed with 1 mL of a PBS solution including 0.05% by weight of Tween 20 to remove the excess first VHH antibody and glucosamine. In this way, a sensor substrate in which the first VHH antibody and glucosamine were immobilized on the base material via the SAM was provided.

[1-c] Blocking Treatment Step

On the surface of the sensor substrate provided in the above step [1-b], 1 mL of a solution (AD solution) provided by 5-fold diluting a blocking agent including bovine serum albumin as a main component with a PBS solution was added to perform a blocking treatment for preventing non-specific adsorption. In this way, the sensor substrate according to the inventive example 1 was provided.

Inventive Example 2

The same procedure as in the inventive example 1 was performed, except that 10% (w/v) trehalose dihydrate was added to the AD solution in the above step [1-c]. In this way, a sensor substrate according to the inventive example 2 was provided.

Comparative Example 1

The same procedure as in the inventive example 1 was performed, except that 1% (w/v) of D(+)-glucosamine hydrochloride was not added in the above step [1-b]. In this way, a sensor substrate according to the comparative example 1 was provided.

Comparative Example 2

The same procedure as in the inventive example 1 was performed, except that 10% (w/v) of trehalose dihydrate (hereinafter, sometimes referred to as trehalose) was added in place of 1% (w/v) of D(+)-glucosamine hydrochloride in the above step [1-b]. In this way, a sensor substrate according to the comparative example 2 was provided.

Comparative Example 3

The same procedure as in the inventive example 1 was performed, except that 1% (w/v) of D(+)-glucosamine hydrochloride was not added in the above step [1-b] and that 10% (w/v) of trehalose dihydrate was added to the AD solution in the above step [1-c]. In this way, a sensor substrate according to the comparative example 3 was provided.

[2] Drying Step

Each sensor substrate provided in the above step [1] was dried with an air gun.

[3] Storage Step

The sensor substrates dried in the above step [2] and silica gel were put in a sealed container and stored at 40° C. for 1 week.

[4] Evaluation of Non-Specific Adsorption

Figure 15:
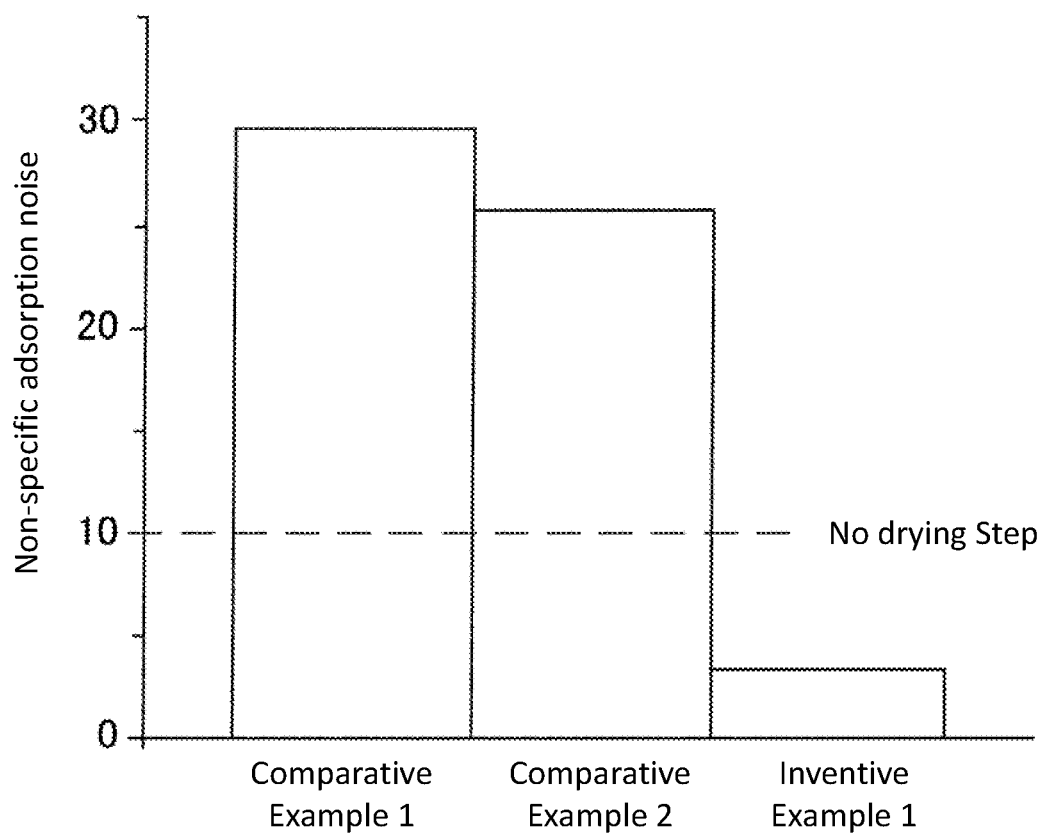
FIG. 15 is a diagram showing detection results of non-specific adsorption noise after the sensor substrates provided in the inventive example 1, the comparative example 1, and the comparative example 2 were subjected to a drying step.

After the sensor substrates provided in the inventive example 1, the comparative example 1 and the comparative example 2 were dried in the above-mentioned step [2], non-specific adsorption noise was detected according to the following procedure to evaluate a degree of the non-specific adsorption (i.e., a degree of occurrence of the non-specific adsorption). The results are shown in FIG. 15.

Figure 16:
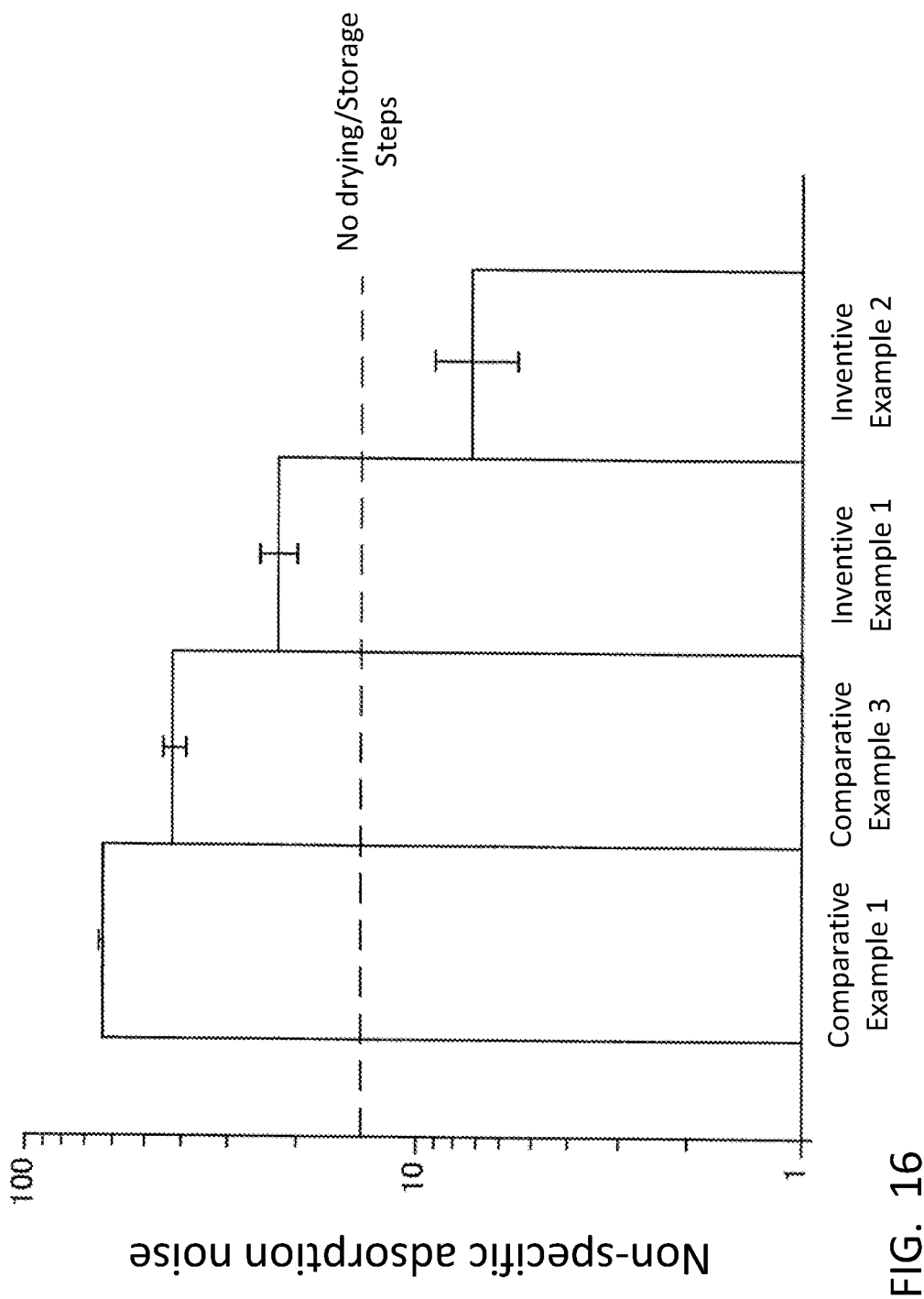
FIG. 16 is a diagram showing detection results of the non-specific adsorption noise after the sensor substrates provided in the inventive example 1, the inventive example 2, the comparative example 1, and the comparative example 3 were subjected to the drying step and a storage step.

In addition, for the sensor substrates provided in the inventive example 1, the inventive example 2, the comparative example 1, and the comparative example 3, after the storage in the above step [3], non-specific adsorption noise was detected according to the following procedure, to evaluate a degree of the non-specific adsorption. The results are shown in FIG. 16.

[4-a] Step of Adsorbing Labeled Antibody Non-Specifically on Surface of Substrate A second VHH antibody having the NP as an antigen was labeled with an organic fluorescent dye having an emission wavelength of 800 nm to prepare a labeled antibody. Subsequently, 0.5 mL of PBS solution including 0.5 μg/mL of the labeled antibody was added to the surface of the sensor substrate and reacted for 60 minutes. In this way, the labeled antibody was non-specifically adsorbed on the surface of the sensor substrate. Next, the sensor substrate was washed 3 times with 1 mL of a PBS solution including 0.05% by weight of Tween 20 to remove the excess labeled antibody.

[4-b] Noise Detection Step

The sensor substrate on which the labeled antibody was adsorbed non-specifically in the above step [4-a] was irradiated with a laser beam having a wavelength of 785 nm to excite the organic fluorescent dye of the labeled antibody absorbed non-specifically on the surface of the sensor substrate. Subsequently, the intensity of the fluorescence (hereinafter, referred to as fluorescence intensity) at a wavelength of 800 nm emitted by the excited organic fluorescent dye was measured.

Non-specific adsorption noise was calculated using the following formula (1). In the formula (1), the signal intensity is a peak value of a spectrum of the measured fluorescence intensity, and the base intensity is a base value of the spectrum of the fluorescence intensity.

$$\text{Non-specific adsorption noise} = \text{Signal intensity} - \text{Base intensity} \quad \text{Formula (1)}$$

[5] Evaluation of Sandwich Assay

Figure 17:
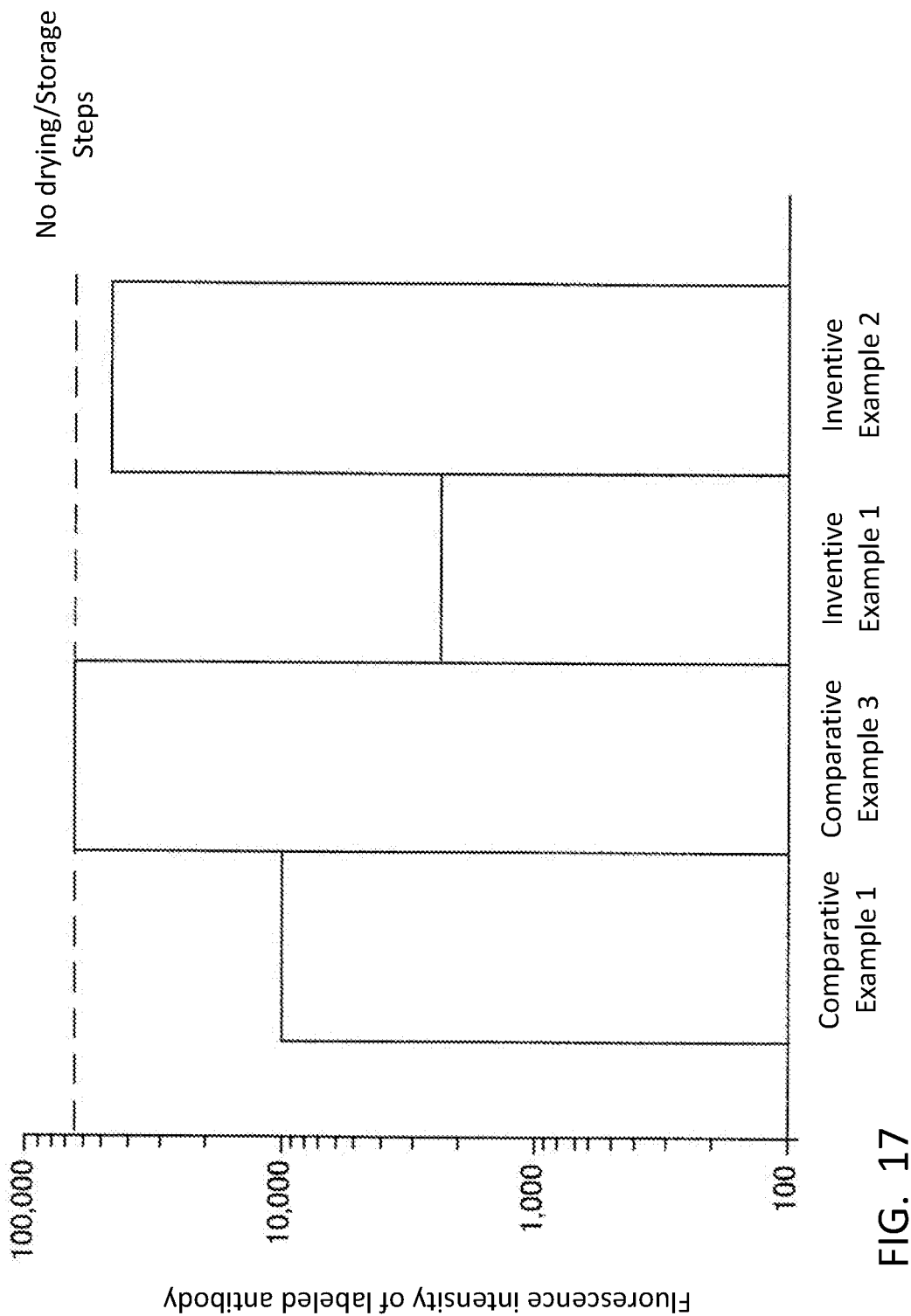
FIG. 17 is a diagram showing results of sandwich assay after the sensor substrates provided in the inventive example 1, the inventive example 2, the comparative example 1, and the comparative example 3 were subjected to the drying step and the storage step.

For the sensor substrates provided in the inventive example 1, the inventive example 2, the comparative example 1 and the comparative example 3, after dried in the above step [3], sandwich assay was performed according to the following procedure. The results are shown in FIG. 17.

[5-a] Step of Binding Analyte Specifically to First VHH

As the analyte, an NP, which was the antigen of the first VHH antibody, was used. An AD solution including 1 nM of NP (hereinafter, referred to as a sample solution) was prepared, 0.5 mL of the sample solution was added onto the surface of the sensor substrate, and the reaction was performed for 60 minutes. In this way, the first VHH antibody and the NP were bound to each other. Subsequently, the surface was washed three times with 1 mL of a PBS solution including 0.05% by weight of Tween 20 to remove the excess NP and blocking agent. As a result, a sensor substrate in which the NP was captured by the first VHH antibody was provided.

[5-b] Step of Specifically Binding Analyte Captured by First VHH Antibody and Labeled Antibody Onto the surface of the sensor substrate in which NP was captured by the first VHH antibody in the above step [5-a], 0.5 mL of a PBS solution including the labeled antibody mentioned above in the step [4-a] was added to react for 60 minutes. In this way, the NP captured by the first antibody was bound to the labeled antibody, and a composite having a sandwich structure (first antibody/NP/labeled antibody) in which the NP was sandwiched between the first antibody and the labeled antibody was formed. Next, this sensor substrate was washed three times with 1 mL of a PBS solution including 0.05% by weight of Tween 20 to remove the excess labeled antibody.

[5-c] Signal Detection Step

The sensor substrate on which the composite was formed in the above step [5-b] was irradiated with a laser beam having a wavelength of 785 nm to excite the organic fluorescent dye of the labeled antibody. Subsequently, the intensity of the fluorescence (hereinafter, referred to as fluorescence intensity) at a wavelength of 800 nm emitted by the excited organic fluorescent dye was measured. Using the following formula (2), the fluorescence intensity of the labeled antibody was calculated. In the formula (2), the signal intensity is a peak value of a spectrum of the measured fluorescence intensity, and the base intensity is a base value of the spectrum of the fluorescence intensity.

$$\text{Fluorescence intensity of labeled antibody} = \text{Signal intensity} - \text{Base intensity} \quad \text{Formula (2)}$$

(Results)

The following four kinds of sensor substrates were provided by the methods described in the inventive examples 1 and 2 and the comparative examples 1 to 3.

1) The sensor substrate of the inventive example 1 is a sensor substrate in which sugar (here, glucosamine) has been immobilized on the surface of the base material by a chemical bond.

2) The sensor substrate of the inventive example 2 is a sensor substrate in which sugar (here, glucosamine) has been immobilized on the surface of the base material by a chemical bond and which has been produced by adding sugar (here, trehalose) in the blocking treatment step.

3) The sensor substrate of the comparative example 1 is a sensor substrate produced by adding no sugar along with the first VHH antibody.

4) The sensor substrate of the comparative example 2 is a sensor substrate produced by adding, together with the first VHH antibody, a kind of sugar (here, trehalose) that is not bound to the surface of the base material by a chemical bond.

5) The sensor substrate of the comparative example 3 is a sensor substrate produced by adding sugar (here, trehalose) in the blocking treatment step without adding sugar along with the first antibody.

As a result of evaluating the degree of non-specific adsorption from the magnitude of the non-specific adsorption noise detected for each of the sensor substrates of the inventive example 1, the inventive example 2, and the comparative examples 1 to 3, the following matters were found. If sugar is immobilized on the carboxyl group terminal of the SAM of the sensor substrate by a chemical bond, non-specific adsorption can be suppressed, even if the sensor substrate is placed in an environment where the sensor substrate is easily dried. This is because not only the deterioration of the first VHH antibody due to the drying of the SAM can be suppressed but also the non-specific adsorption in the SAM can be suppressed by immobilizing the sugar on the SAM.

Hereinafter, [a] evaluation of the non-specific adsorption of the sensor substrate in a case where the drying step is performed, and [b] evaluation of the non-specific adsorption of the sensor substrate in a case where the drying step and the storage step are performed will be described.

[a] Evaluation of Non-Specific Adsorption of Sensor Substrate in a case where drying step is performed FIG. 15 is a diagram showing the detection results of the non-specific adsorption noise after the sensor substrates provided in the inventive example 1, the comparative example 1 and the comparative example 2 were subjected to the above drying step [2]. The dashed line shown in FIG. 15 indicates the magnitude of the specific adsorption noise in a case where the drying step [2] is not performed on the sensor substrate provided in the comparative example 1.

First, a change in the non-specific adsorption noise in a case where the drying step is performed on the sensor substrate of the comparative example 1 in which sugar was not disposed on the surface of the base material will be described.

As shown in FIG. 15, as can be seen from comparison of the case where the drying step was performed on the sensor substrate of the comparative example 1 (the comparative example 1 in FIG. 15) to the case where the drying step was not performed ("No drying step" indicated by the broken line), the non-specific adsorption noise of the comparative example 1 was approximately 3 times as much as than the non-specific adsorption noise without the drying step. This is probably because the first antibody was deteriorated due to the drying, and the second antibody labeled with the fluorescent substance (hereinafter, labeled antibody) was adsorbed non-specifically to the deteriorated site.

Subsequently, with regard to the case where a sensor substrate was produced by adding the first antibody and the first sugar molecule, the sensor substrate of the inventive example 1 and the sensor substrate of the comparative example 2 are compared with each other. Both the sensor substrate of the inventive example 1 and the sensor substrate of the comparative example 2 have sugar molecules disposed on the surface of the base material; however, differ in the following points. In the sensor substrate of the inventive example 1, the sugar molecules are immobilized on the surface of the base material by a chemical bond, whereas in the sensor substrate of the comparative example 2, the sugar molecules are disposed on the surface of the base material without a chemical bond.

As shown in FIG. 15, the non-specific adsorption noise of the comparative example 2 was approximately 9 times as much as the non-specific adsorption noise of the inventive example 1. The sugar molecule used in the comparative example 2 is trehalose, which has a plurality of hydroxy groups, and has a high moisture retention effect. However, since the hydroxy group does not form a chemical bond with the surface of the base material, namely, the carboxyl group of the SAM disposed on the substrate, the sugar molecule (trehalose) is not immobilized on the surface of the base material by a chemical bond. As a result, when the AD solution is added onto the surface of the sensor substrate in the blocking treatment step [1-c], trehalose is washed away from the surface of the sensor substrate. As a result, it is conceivable that the sensor substrate of the comparative example 2 fails to be provided sufficiently with the moisture retention effect generated with the sugar molecules and that the deterioration of the first antibody generated due to drying fails to be suppressed.

The conceivable reason why the non-specific adsorption noise of the sensor substrate of the comparative example 2 is smaller than the non-specific adsorption noise of the sensor substrate of the comparative example 1 which has been produced without adding sugar molecules will be described below. In the sensor substrate of the comparative example 2, it is conceivable that the trehalose was not completely washed away with the AD solution, and that a small amount of trehalose remained. As a result, it is conceivable that a slight moisture retention effect was provided, and that the deterioration of the first antibody was slightly suppressed.

On the other hand, the sugar molecule used in the inventive example 1 is glucosamine and has a plurality of hydroxy groups and one amino group. Similarly to trehalose, glucosamine also has a high moisture retention effect, since glucosamine has the plurality of the hydroxy groups. However, unlike trehalose, glucosamine has an amino group in the molecule thereof, and thus forms a chemical bond with the carboxyl group of the SAM disposed on the substrate. As a result, glucosamine is immobilized on the surface of the base material by the chemical bond. Therefore, even if the AD solution is added onto the surface of the sensor substrate in the blocking treatment step [1-c], the glucosamine remains on the surface of the sensor substrate without being washed away from the surface of the sensor substrate. Therefore, it is conceivable that the sensor substrate of the inventive example 1 had a moisture retention effect sufficiently due to the sugar molecules and that the deterioration of the first antibody generated due to drying was suppressed in the sensor substrate of the inventive example 1.

Subsequently, as can be seen from comparison of the sensor substrate of the inventive example 1 to the sensor substrate of "no drying step" indicated by the broken line, the non-specific adsorption noise of the sensor substrate of the inventive example 1 is approximately one-third times as much as that of the sensor substrate of "no drying step". This is probably because the sensor substrate of the inventive example 1 not only can suppress the deterioration of the first antibody generated due to drying, but also can suppress the non-specific adsorption between the SAM and the labeled antibody, so that the non-specific adsorption noise was further suppressed. The reason therefor will be described below.

In the sensor substrate of the inventive example 1, since the carboxyl group of the SAM and the amino group of glucosamine form the chemical bond, glucosamine is immobilized on the gap part where the first antibody is not immobilized on the surface of the SAM. Therefore, the labeled antibody is difficult to adsorb non-specifically on the surface of the SAM. Furthermore, the sensor substrate of the inventive example 1 protects the first antibody from drying by immobilizing the glucosamine on the surface of the SAM by the chemical bond. Therefore, the sensor substrate of the inventive example 1 can suppress the deterioration of the first antibody generated due to drying, even when the drying step is performed.

On the other hand, in the sensor substrate of "no drying step", the carboxyl group on the surface of the SAM is present in a free state, so that the labeled antibody is likely to be adsorbed non-specifically on the surface of the SAM. Since no drying step is performed for the sensor substrate of "no drying step", the surface of the base material is covered with the AD solution. Therefore, the deterioration of the first antibody generated due to drying is not considered.

As described above, the sugar molecules are immobilized on the surface of the base material by the chemical bond, so that even if the sensor substrate is washed, the sugar molecules are not washed away from the surface of the base material, and the moisture retention effect of the sugar molecules is sufficiently maintained. In this way, the sugar molecules were held on the surface of the base material, and deterioration of the first antibody generated due to drying is allowed to be further suppressed. Furthermore, since the sugar molecule is immobilized in the gap part where the first antibody is not immobilized on the surface of the base material, not only the non-specific adsorption in the deteriorated part of the first antibody but also the non-specific adsorption in the gap part is allowed to be suppressed.

[b] Evaluation of Non-Specific Adsorption of Sensor Substrate in a case where drying step and storage step are performed FIG. 16 is a diagram showing the detection results of the non-specific adsorption noise after the sensor substrates of the inventive example 1, the inventive example 2, the comparative example 1, and the comparative example 3 were subjected to the drying step [2] and the storage step [3]. The broken line shown in FIG. 16 shows the non-specific adsorption noise in a case where the drying step [2] and the storage step [3] were not performed for the sensor substrate of the comparative example 1.

For each of the sensor substrates of the inventive example 1, the inventive example 2, the comparative example 1, and the comparative example 3, the degree of non-specific adsorption was evaluated from the magnitude of the detected non-specific adsorption noise. As a result, the present inventors found the following matters. If the sugar molecules are immobilized on the SAM of the sensor substrate by a chemical bond, and the sugar molecules are disposed at least on the surface of the first VHH antibody, even if the sensor substrate is placed in a dry environment, the non-specific adsorption is allowed to be suppressed. This is because, by immobilizing the sugar molecules on the SAM, not only the deterioration of the first VHH antibody generated due to drying can be suppressed; but also the non-specific adsorption in the SAM is allowed to be suppressed. In addition, this is because the deterioration of the first VHH generated due to drying is allowed to be further suppressed by disposing the sugar molecules at least on the surface of the first VHH antibody.

Hereinafter, the present examples will be described in more detail with reference to the results shown in FIG. 16.

FIG. 16 is a diagram showing the detection results of the non-specific adsorption noise after the sensor substrates provided in the inventive example 1, the inventive example 2, the comparative example 1, and the comparative example 3 were subjected to the drying step [2] and the storage step [3]. The broken line shown in FIG. 16 indicates the non-specific adsorption noise in a case where the drying step [2] and the storage step [3] were not performed for the sensor substrate of the comparative example 1.

First, changes in the non-specific adsorption noise in a case where the drying step and the storage step are performed for the sensor substrate of the comparative example 1 produced without adding the first sugar molecule and the second sugar molecule will be described.

As shown in FIG. 16, as can be seen from comparison of a case where the drying step and the storage step were performed for the sensor substrate of the comparative example 1 (the comparative example 1 in FIG. 16) to a case where the drying step and the storage step were not performed ("No drying/storage step" shown by the broken line in FIG. 16), the non-specific adsorption noise of the sensor substrate of the comparative example 1 is approximately five times as much as the non-specific adsorption noise of the sensor substrate of "No drying/storage step". This is probably because the first VHH antibody (hereinafter, referred to as the first antibody) was deteriorated since the sensor substrate of the comparative example 1 was dried by the drying step and the storage step, and the labeled antibody was non-specifically adsorbed at the deteriorated site.

Next, change in non-specific adsorption noise depending on the presence or absence of the sugar molecule will be described by comparing the sensor substrates of the inventive example 1, the inventive example 2, and the comparative example 3 produced by adding at least one of the first sugar molecule and the second sugar molecule (hereinafter, simply referred to as "sugar molecule") to the sensor substrate of the comparative example 1 produced without adding the first sugar molecule and the second sugar molecule.

As shown in FIG. 16, the sensor substrates of the inventive example 1, the inventive example 2, and the comparative example 3 had less non-specific adsorption noise than the sensor substrate of the comparative example 1. Therefore, it was found that non-specific adsorption is suppressed if the sugar molecules are present on the surface of the sensor substrate. As a result, it is conceivable that, in the sensor substrate produced by adding the sugar molecules, even when the sensor substrate is dried, hydroxyl groups (OH groups) of the sugar molecules act in place of water molecules, and that the deterioration of the first antibody generated due to drying is suppressed.

The non-specific adsorption noise of the sensor substrate of the comparative example 3 was approximately ⅔ times as much as the non-specific adsorption noise of the sensor substrate of the comparative example 1. In the sensor substrate of the comparative example 3, the second sugar molecule (trehalose) is present on the surface of the base material in such a way that is disposed at least on the surface of the first antibody. Trehalose does not have a functional group capable of forming a chemical bond with the carboxyl group terminal of the SAM; however, acts in place of a water molecule, since trehalose has a plurality of hydroxy groups. Therefore, it is conceivable that the deterioration of the first antibody generated due to drying was suppressed by disposing the trehalose on the surface of the first antibody.

The non-specific adsorption noise of the sensor substrate of the inventive example 1 was approximately ⅓ times as much as the non-specific adsorption noise of the sensor substrate of the comparative example 1. In the sensor substrate of the inventive example 1, the first sugar molecule (glucosamine) is immobilized by a chemical bond on the surface of the base material, more specifically, to the gap part where the first antibody is not immobilized on the surface of the base material. Since glucosamine is an amino sugar having an amino group, glucosamine forms a covalent bond with the carboxyl group terminal of the SAM. As described above, it is conceivable that, since the first sugar molecule was immobilized on the surface of the base material by the chemical bond, not only the deterioration of the first antibody generated due to drying was suppressed, but also non-specific binding which might occur at the gap part on the surface of the base material was suppressed.

The non-specific noise of the sensor substrate of the inventive example 2 was approximately ¹⁄₁₀ times as much as the non-specific adsorption noise of the sensor substrate of the comparative example 1. In the sensor substrate of the inventive example 2, the first sugar molecule (glucosamine) is immobilized on the surface of the base material by the chemical bond, and the second sugar molecule (trehalose) is disposed at least on the surface of the first antibody. As described in the inventive example 2, it is conceivable that, since the sensor substrate is produced by adding both the first sugar molecule which is immobilized on the surface of the base material and the second sugar molecule which is disposed at least on the surface of the first antibody, the first sugar molecule protects a lower part of the first antibody, which forms the chemical bond with the SAM, and the second sugar molecule protects an upper part of the first antibody, which captures the NP of the first antibody. Therefore, it is conceivable that the effect of protecting the first antibody from drying is improved and that deterioration of the first antibody generated due to drying is further suppressed, as compared to the case where either one of the first sugar molecule and the second sugar molecule is added.

In addition, the sensor substrates of the inventive example 1, the inventive example 2, and the comparative example 3 is compared to the sensor substrate of "no drying/storage steps". The non-specific adsorption noise of the sensor substrate of the inventive example 1 and the comparative example 3 was greater than the non-specific adsorption noise of the sensor substrate of "no drying/storage steps". On the other hand, the non-specific adsorption noise of the sensor substrate of the inventive example 2 was smaller than the non-specific adsorption noise of the sensor substrate of "no drying/storage steps". The sensor substrate of "no drying/storage steps" is a sensor substrate in which the sensor substrate of the comparative example 1 produced without adding sugar molecules has not been subjected to the drying step and the storage step. The sensor substrate "no drying/storage steps" has free carboxyl groups on the surface of the SAM, so that the blocking agent included in the AD solution blocks the labeled antibody from being adsorbed non-specifically on the surface of the SAM. The non-specific adsorption noise of the sensor substrate of the inventive example 2 was approximately ½ times as much as the non-specific adsorption noise of the sensor substrate of "no drying/storage steps". Therefore, it is conceivable that, in addition to the effect of suppressing the deterioration of the first antibody generated due to drying, there is also an effect of suppressing the non-specific adsorption on the surface of the SAM by chemically binding the free carboxyl group terminal of the SAM to the first sugar molecule. In this way, it is conceivable that the non-specific adsorption noise was further suppressed.

Hereinafter, the evaluation of the sandwich assay [5] will be described using the sensor substrate after the storage step.

As a result of the sandwich assay for each of the sensor substrates of the inventive example 1, the inventive example 2, the comparative example 1 and the comparative example 3, the present inventors found the following matters.

When sugar is immobilized on the SAM of the sensor substrate by the chemical bond and the sugar is disposed at least on the surface of the first antibody, the non-specific adsorption is allowed to be suppressed, even if the sensor substrate is placed in an environment where the sensor substrate is easily dried. This is because, by immobilizing the sugar on the SAM, not only the deterioration of the first antibody generated due to drying is allowed to be suppressed but also the non-specific adsorption in the SAM is allowed to be suppressed. In addition, this is because the deterioration of the first antibody generated due to drying is allowed to be further suppressed by disposing the sugar molecule at least on the surface of the first antibody.

Hereinafter, the present examples will be described in more detail with reference to the results shown in FIG. 17.

FIG. 17 is a diagram showing the results of the sandwich assay after the sensor substrates provided in the inventive example 1, the inventive example 2, the comparative example 1, and the comparative example 3 were subjected to the drying step [2] and the storage step [3]. The broken line shown in FIG. 17 indicates the result of the sandwich assay when the drying step [2] and the storage step [3] were not performed for the sensor substrate provided in the comparative example 1.

First, the results of the sandwich assay in a case where the drying step and the storage step are performed for the sensor substrate of the comparative example 1 produced without adding the first sugar molecule and the second sugar molecule will be described.

As shown in FIG. 17, as can be seen from comparison of a case where the drying step and the storage step were performed for the sensor substrate of the comparative example 1 (the comparative example 1 in FIG. 17) to a case where the drying step and the storage step were not performed ("No drying/storage step" shown by the broken line in FIG. 17), the fluorescence intensity detected on the sensor substrate of the comparative example 1 approximately ⅕ times as much as the fluorescence intensity detected on the sensor substrate of "no drying/storage step". This is probably because the sensor substrate of the comparative example 1 was dried during the drying step and the storage step, the first antibody, especially the binding site of the first antibody and the antigen, was deteriorated, and an ability to capture an antigen was lowered.

Subsequently, as can be seen from comparison of the sensor substrate of the inventive example 1, the inventive example 2 and the comparative example 3 produced by adding the sugar molecules to one another, among these three sensor substrates, the fluorescence intensity detected on the sensor substrates of the inventive example 2 and the comparative example 3 were equivalent to the fluorescence intensity detected on the sensor substrate "no drying/storage steps". On the other hand, the fluorescence intensity detected on the sensor substrate of the inventive example 1 was approximately ½₂ times as much as the fluorescence intensity detected on the sensor substrates of the inventive example 2 and the comparative example 3. In the sensor substrates of the inventive example 1 and the inventive example 2, the second sugar molecules are disposed at least on the surface of the first antibody. On the other hand, in the sensor substrate of the inventive example 1, the second sugar molecules are not arranged on the surface of the first antibody. In the sensor substrate of the inventive example 1, the first sugar molecules are immobilized on the surface of the base material by a chemical bond. Therefore, it can be seen that, by disposing the second sugar molecules at least on the surface of the first antibody, the deterioration of the first antibody generated due to drying, especially, the deterioration of the binding site of the first antibody capable of binding to the NP (hereinafter, referred to as NP binding site) is suppressed.

Next, as it can be seen from comparison of the sensor substrate of the inventive example 1 to the sensor substrate of the comparative example 1, the fluorescence intensity detected on the sensor substrate of the comparative example 1 was greater than the fluorescence intensity detected on the sensor substrate of the inventive example 1. The sensor substrate of the comparative example 1 has been produced without adding the sugar molecules, and no sugar is immobilized on the surface of the base material. On the other hand, in the sensor substrate of the inventive example 1, the first sugar molecules are immobilized on the surface of the base material by a chemical bond. In the sensor substrate of the inventive example 1, it is conceivable that, since the first sugar molecule is immobilized on the surface of the base material, the non-specific adsorption on the surface of the base material is suppressed. In addition, in the sensor substrate of the inventive example 1, it is conceivable that, since the first sugar molecules protect a part close to the surface of the base material of the first antibody from drying, the deterioration of the part generated due to drying is suppressed. Therefore, it is conceivable that the fluorescence intensity detected on the sensor substrate of the comparative example 1 includes the fluorescence intensity (non-specific adsorption noise) detected by binding the labeled antibody to something other than the NP due to the above-described non-specific adsorption.

Next, the difference in fluorescence intensity between the sensor substrate of the inventive example 2 and the sensor substrate of the comparative example 3 will be considered. The sensor substrate of the inventive example 2 is different from the sensor substrate of the comparative example 3 in that the first sugar molecule is immobilized on the surface of the base material by the chemical bond. It is conceivable that, since the fluorescence intensity detected on the sensor substrate of the comparative example 3 includes the above-described non-specific adsorption noise, the fluorescence intensity is greater than the fluorescence intensity detected on the sensor substrate of the inventive example 2.

As described above, even when the sensor substrate of the inventive example 2 is placed in an environment where the sensor substrate is easily dried, the first sugar molecules are immobilized on the surface of the base material by a chemical bond, and the second sugar molecules are disposed at least on the surface of the first sugar molecules. Therefore, it was found that the deterioration of the first antibody generated due to drying is suppressed, so that the non-specific adsorption in the deteriorated part of the first antibody is suppressed, and the non-specific adsorption on the surface of the base material is suppressed. In addition, it was found that, since the deterioration of the binding site of the first antibody generated due to drying is suppressed, the decrease in the ability of the first antibody to bind to the analyte (namely, the activity of the first antibody) is suppressed. As just described, it was proved that the storage stability of the sensor substrate of the inventive example 2 is improved, since the sensor substrate of the inventive example 2 has the above configuration.

The sensor substrate, the method for manufacturing the sensor substrate, and the detection device according to the present disclosure have been described based on the embodiments and examples. However, the present disclosure is not limited to the embodiments and examples. Without departing from the gist of the present disclosure, various modifications conceived by those skilled in the art have been made in the embodiments and examples, and other forms constructed by combining some constituent elements in the embodiments and examples are also included within the scope of the present disclosure.

Note that the sensor substrate, the method for manufacturing the sensor substrate, and the detection device according to the present disclosure may be used in, for example, a detection system capable of detecting a virus floating in an air. Hereinafter, a detection system will be described as other embodiments.

OTHER EMBODIMENTS

[Outline of Detection System]

Figure 18:
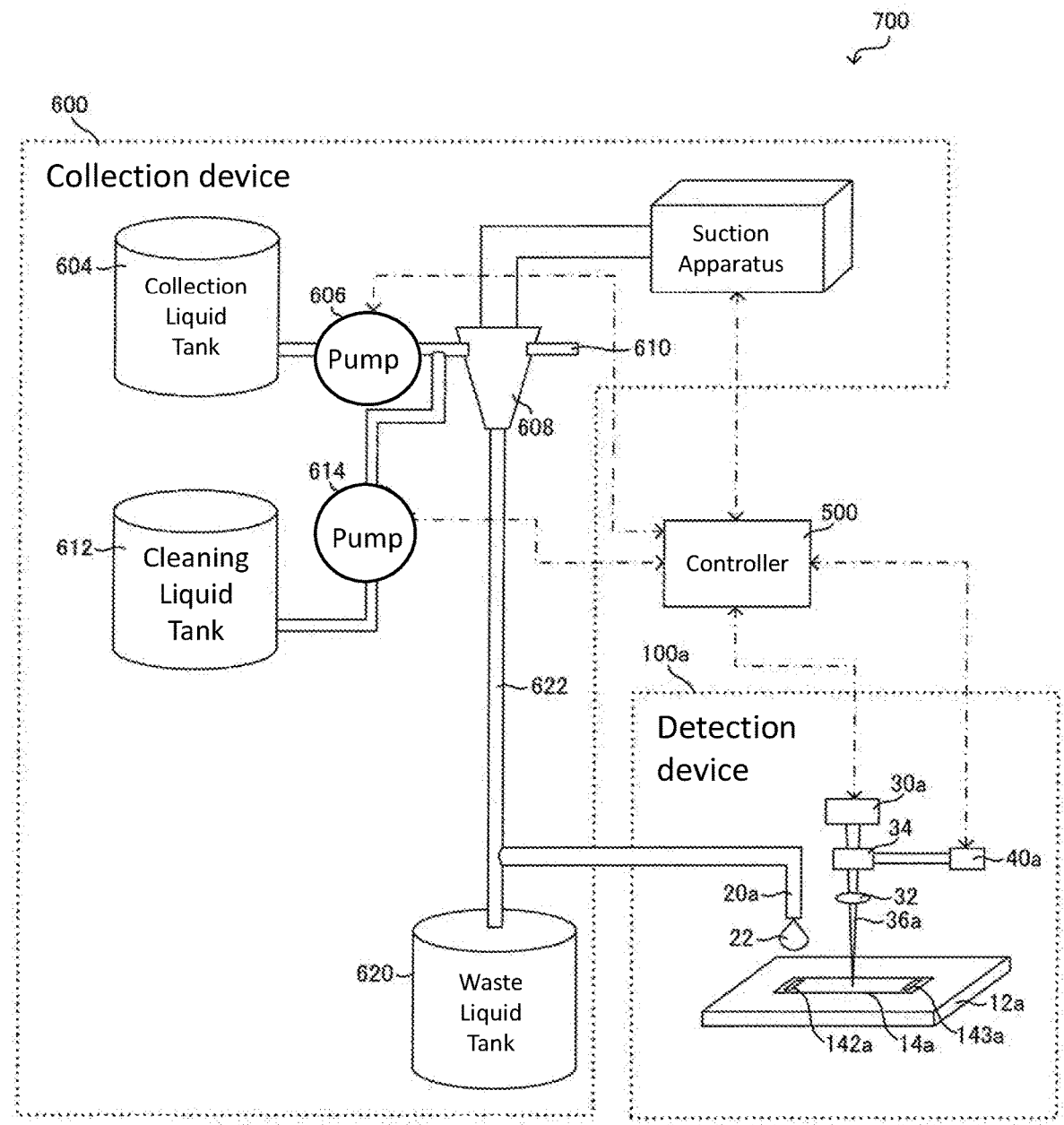
FIG. 18 is a schematic configuration diagram showing one example of a configuration of a detection system according to the present disclosure.

FIG. 18 is a schematic configuration diagram illustrating one example of a configuration of a detection system 700 according to the present disclosure. The detection system 700 is set, for example, in a room which people enter and exit. As shown in FIG. 18, the detection system 700 comprises a collection device 600, a detection device 100a, and a controller 500. Hereinafter, the details of the collection device 600 and the controller 500 will be described. Since the detection device 100a has been described in the first embodiment, the description thereof is omitted here.

[Configuration of Collection Device]

In the collection device 600, fine particles which may include a virus in an air are collected and mixed with a collection liquid. As shown in FIG. 16, the collection device 600 comprises a suction apparatus 602, a collection liquid tank 604, a pump 606, a cyclone 608, an air inlet 610, a cleaning liquid tank 612, a pump 614, and a waste liquid tank 620, and a liquid flow path 622. Hereinafter, each component of the collection device 600 will be described.

The suction apparatus 602 sucks ambient atmospheric air from the air inlet 610. The fine particles that may include a virus floating in the ambient atmosphere air are sucked into the cyclone 608 from the air inlet 610 along with the air.

The pump 606 supplies the collected liquid in the collection liquid tank 604 to the cyclone 608.

The cyclone 608 is connected to the air inlet 610 and the collection liquid tank 604. In the cyclone 608, the fine particles that may include a virus in the air sucked from the air inlet 610 with the suction apparatus 602 and the collected liquid supplied from the collection liquid tank 604 with the pump 606 are mixed with each other. The cyclone 608 is connected to the detection device 100a via the liquid flow path 622. The collected liquid mixed with the fine particles (hereinafter, referred to as a sample) is discharged from the cyclone 608 to the detection device 100a via the liquid flow path 622.

The cleaning liquid tank 612 is a container for containing a cleaning liquid for cleaning the cyclone 608 and the liquid flow path 622. The cleaning liquid tank 612 is connected to the cyclone 608, and the cleaning liquid in the cleaning liquid tank 612 is supplied to the cyclone 608 with the pump 614.

The waste liquid tank 620 is a container for storing unnecessary liquid.

The liquid flow path 622 is a path for guiding the sample output from the cyclone 608 to the detection device 100a.

[Configuration of Controller]

As shown in FIG. 18, the controller 500 controls the operation of the entire detection system 700. In the detection device 100a according to the first embodiment, the controller 50a controls the operation of each part of the detection device 100a. However, in the present embodiment, the controller 500 is different from the controller 50a in that the controller 500 controls the operation of the entire detection system 700. Specifically, the controller 500 controls the collection device 600 and the detection device 100a.

More specifically, the controller 500 controls the start of measurement, causes the suction apparatus 602 to start sucking an ambient air, and causes the pump 606 to supply the collected liquid from the collection liquid tank 604 to the cyclone 608. In this way, the collection liquid and the fine particles are mixed in the cyclone 608, and the sample is supplied from the cyclone 608 to the detection device 100a. Furthermore, the controller 500 causes the light source 30a to emit light and causes the detection part 40a to detect surface-enhanced fluorescence.

For example, the controller 500 can control each pump and supply a predetermined volume of the sample liquid 22 to the detection device 100a under preset conditions based on the input parameters. Furthermore, the controller 500 may have a time measurement function, and information on the time required for each operation may be generated and stored. In addition, the controller 500 may receive a measurement value from the detection device 100a and calculate a temporal change in the concentration of the virus floating in the air on the basis of the measurement value and time information.

The controller 500 is realized by, for example, one or more dedicated electronic circuits. The one or more dedicated electronic circuits may be integrated on one chip, or may be individually formed on a plurality of chips. The controller 500 may be realized by a general-purpose processor (not shown) and a memory (not shown) in which a software program or an instruction has been stored, in place of the one or more dedicated electronic circuits. In this case, the processor functions as the controller 500, when the software program or instruction is executed.

INDUSTRIAL APPLICABILITY

The sensor substrate according to the present disclosure has high storage stability and is useful as a biosensor for research, medical use, and environmental measurement. In addition, the sensor substrate and the detection device using the sensor substrate according to the present disclosure can be applied not only to a non-competitive method (sandwich immunoassay method) but also to a competitive method and a gene detection method using hybridization.

REFERENCE SIGNS LIST 10a, 10b Sensor substrate
12a, 12b Sensor device
14a, 14b Sensor cell
20a Introduction part
22 Sample liquid
30a Application part (light source)
30b Application part (second introduction part)
32 Lens
34 Beam splitter
36a Inducer (excitation light)
36b Inducer (substrate)
40a, 40b Detection part
50a, 50b Controller
100a, 100b Detection device
102a Base material
110a Detection region
114 First specific-binding substance
116 First sugar molecule
118 Second sugar molecule
141a Flow path
142a Supply hole
143a Discharge hole
144a Lid part
222 Analyte
224 Second specific-binding substance
226a, 226b Labeled substance
362b Coloring substance
500 Controller
600 Collection device
602 Suction apparatus 604 Collection liquid tank
606 Pump
608 Cyclone
610 Air inlet
612 Cleaning liquid tank
614 Pump
620 Waste liquid tank
622 Liquid flow path
700 Detection system
1020 Substrate
1022 Organic membrane

The invention claimed is:

1. A sensor substrate, comprising:
a base material;
a first specific-binding substance that has a property of binding specifically to an analyte and is immobilized on a surface of the base material; and
a first sugar molecule which is an amino sugar molecule,
wherein the first sugar molecule consists of a monosaccharide,
the first sugar molecule is immobilized by an amide bond on the surface of the base material, and
the monosaccharide includes D-galactosamine, sialic acid, aminouronic acid, or muramic acid.

2. The sensor substrate according to claim 1, wherein
the base material includes a substrate and an organic membrane disposed on the substrate;
the first specific-binding substance is immobilized on the surface of the base material through binding to the organic membrane; and
the first sugar molecule is immobilized on the organic membrane by the amide bond.

3. The sensor substrate according to claim 2, wherein the organic membrane is a self-assembled monolayer.

4. The sensor substrate according to claim 1, further comprising:
a blocking agent covering at least a part of the surface of the base material.

5. The sensor substrate according to claim 1, further comprising:
a second sugar molecule,
wherein the second sugar molecule is disposed at least on a surface of the first specific-binding substance.

6. The sensor substrate according to claim 5, wherein the second sugar molecule has a chemical structure different from that of the first sugar molecule.

7. A detection device, comprising:
the sensor substrate according to claim 1;
an introduction part through which a second specific-binding substance and a sample are introduced to the sensor substrate, wherein the second specific-binding substance has a property of binding specifically to an analyte and is labeled with a labeled substance, and the sample contains the analyte;
an application part for applying an inducer capable of inciting a signal from the labeled substance to the sensor substrate to which the second specific-binding substance and the sample have been introduced; and
a detection part for detecting the analyte on a basis of the signal emitted from the labeled substance,
wherein the introduction part, the application part, and the detection part are placed above the sensor substrate.

8. The sensor substrate according to claim 5, wherein the second sugar molecule has no carboxyl group and no amino group.

* * * * *